United States Patent
Ludwig

(10) Patent No.: US 7,700,726 B2
(45) Date of Patent: Apr. 20, 2010

(54) HIV ANTISENSE PROTEINS

(76) Inventor: Linda B. Ludwig, 861 Main St., East Aurora, NY (US) 14052

( * ) Notice: Subject to any disclaimer, the term of this patent is extended or adjusted under 35 U.S.C. 154(b) by 1152 days.

(21) Appl. No.: 11/076,728

(22) Filed: Mar. 10, 2005

(65) Prior Publication Data

US 2006/0024321 A1 Feb. 2, 2006

Related U.S. Application Data

(60) Division of application No. 10/135,545, filed on Apr. 30, 2002, now abandoned, which is a continuation-in-part of application No. 09/249,542, filed on Feb. 12, 1999, now Pat. No. 6,392,029, and a continuation-in-part of application No. 08/853,703, filed on May 9, 1997, now Pat. No. 5,919,677.

(60) Provisional application No. 60/074,640, filed on Feb. 13, 1998.

(51) Int. Cl.
*C07K 14/155* (2006.01)
*C07K 14/16* (2006.01)
*C07K 16/08* (2006.01)
*C07K 16/10* (2006.01)

(52) U.S. Cl. .................. 530/350; 530/387.1; 530/388.3; 530/388.35

(58) Field of Classification Search ................. 530/300, 530/350

See application file for complete search history.

(56) References Cited

OTHER PUBLICATIONS

Linda B Ludwig et al., Human Immunodeficiency Virus-Type 1 LTR DNA contains an intrinsic gene producing antisense RNA and protein products. Retrovirology 2006, vol. 3, No. 80, no pages listed. doi:10.1186/1742-4690-3-80.*

* cited by examiner

*Primary Examiner*—Mary E Mosher
*Assistant Examiner*—Myron G Hill

(57) ABSTRACT

Disclosed is a novel HIV gene comprising a set of open reading frames encoded with the template as the plus strand of the proviral DNA, and located in the region of HIV-1 long terminal repeat. The genes encode a set of antisense proteins, (HAPs) as well as smaller proteins, related to, and containing structural motif resembling that of chemokine proteins. Depending upon the ribosomal frameshift, a plurality of proteins may be translated from the antisense RNA. The smaller proteins have similarity with chemokine SDF-1 and may play a role as a cofactor with gp120 in the binding to and entry of HIV to a target cell.

4 Claims, 21 Drawing Sheets

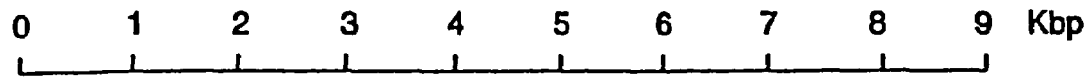
HIV-1
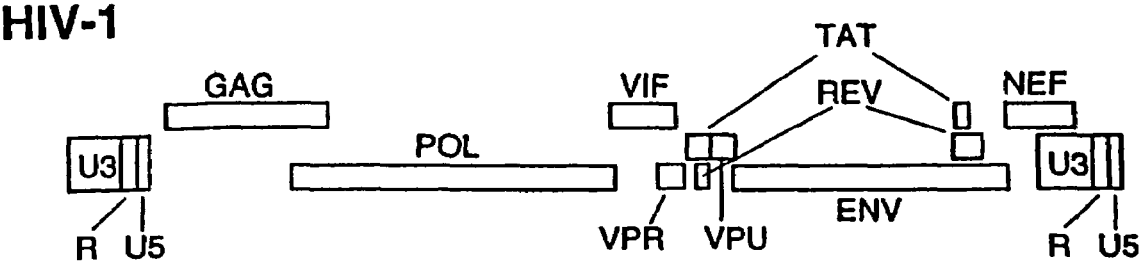
FIG. 1a
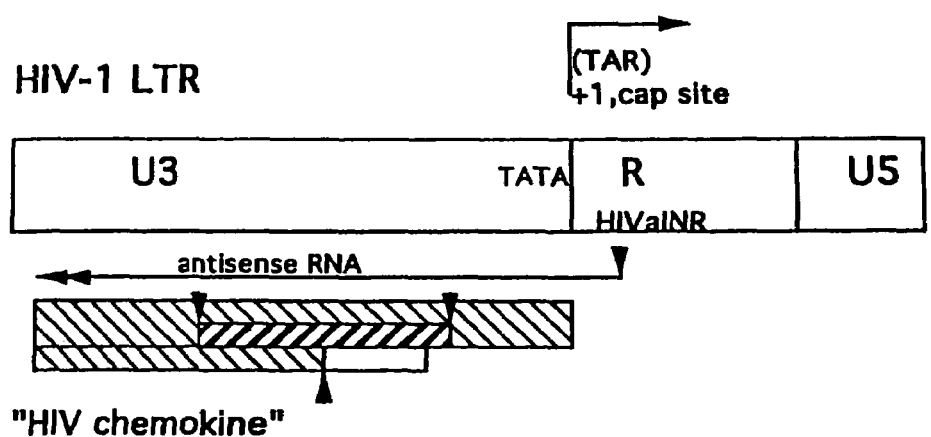
FIG. 1b

```
HIVaINRsO   -M-SA-VFVVLRMQ-LSGHVTKCRR--LSNFHTNTSP--SGSSI--PCW-   39
SDF-1       -M-QAKVVAVLA---LVLAAL-CI--------SDGKP-VSLSYR-CPGR-   33
IP-10       MNQTAILICCLIFLTLSGIQGV--------------P-LSRTVR-CTCI-   33
IL-8        -MTSKLAVAILAAFLISAAL--CEGAVL--------P-RSAKELRCQCI-   37
I-309       ---MQIITTALVCILLAGMWPEDVD---------SK--SMQVPFSRCCF   35
RANTES      ---MKVSAARLAVI-LIATAL-CAPA--SA-----SP---YSSDTTPCCF   35
MIP-1b      --MKLCVT-VLSLLMLVAAF--CSPA-LS------AP--MGSDPPTACCF   36
MIP-1a      MQVSTAALAVLLCTMAL-----CNQV-LS------AP--LAADTPTACCF   36
Lymphotac   -------MRLLILA-LLGI---CSLT-AYIVEGVGS---EVSDKRT-CVS   34

HIVaINRsO   ----LIGC--N--KLFFSPY-LASST-CSGSTGT-N-LKHHP-KVSGYLI   76
SDF-1       FFESHIARA-NV-KHLKI---LNTPN-CALQIVA-R-LKNMMRQV-C-ID   73
IP-10       SISNQPVNPRSLEKLEIIP---ASQF-CPRVEIIATMKKKGEKR--C-LN   76
IL-8        ---KTYSKPFHP-KFIKELRVIESGPHCANTEIIV-KLSDGREL--C-LD   79
I-309       ---SFAEQEI--PLRAILCYRNTSSI-CSNE-GLIFKLKRGKE-A-CALD   76
RANTES      -AYIARPLPRAHIKEY--FY--TSGK-CSNPAVVFVTRKNR--QV-C-AN   75
MIP-1b      -SYTARKLPRN----FVVDYYETSSL-CSQPAVVFQ-TKRSK-QV-C-AD   76
MIP-1a      -SYTSRQIPQN----FIADYFETSSQ-CSKPSVIF-LTKRGR-QV-C-AD   76
Lymphotac   ----LTTQRLPV--SRIKTYT-ITEG--SLRAVIFI-TKRGL-KV-C-AD   71

HIVaINRsO   PGPG-V---------------------------    81
SDF-1       PKLKWIQEYLEKALNKRLKM-------------    93
IP-10       PESKAIKNLLKAVSKEMSKRSP-----------    98
IL-8        PKENWVQRVVEKFLKRAENS-------------    99
I-309       -TVGWVQRHRKML--------------------    88
RANTES      PEKKWVREYINSLEMS-----------------    91
MIP-1b      PSESWVQEYVYDLELN-----------------    92
MIP-1a      PSEEWVQKYVSDLELSA----------------    93
Lymphotac   PQATWVRDVVRSMDRKSNTRNNMIQTKPTGTQQSTNTAVTLTG    114
```

FIG. 7

Potential HIV aINR generated antisense ORFS from TCLA, macrophage-tropic primary viral or patient CNS vs LN/Sp tissue viral LTR sequences (+1/-1 ribosomal frameshift(s))
```
SF2         MQHLRARHSPVPPRPRLPGKSPAESPL (+1) RKLDVSSLCSTPDAALGP
YU2         MQHLRARHSPVPPRPRFPGKSPAESPL (+1) RKLEVISSCSTPDAALGP
JR-FL       MQHLRARHSPVPPRPRLPGKSPVESPL (+1) RKLDVSSPCSTPDAALGP
(Pt)CNS     MQHLRARHSPVPPRPHLPGKSPAESPL (+1)RKFDVISSCSTPDAALGP
(Pt)LN/SP   MQHLRARHSPVPPSPRLPGKSPAESPL(+1)RKL(A)GVSSSCSSPDAALG
                                           (GVSSG)

SF2         CDEMLVCCQTSTLTLLSPRPPSHAGS(-1)IGCNKLLFSPSLASSTFSGS
YU2         RDEMLVCCQTSTLTLLSPGHPFHAGS(-1)IGCNKQLFSPALASSIFSGS
JR-FL       RDEMLACCQTSTLTLPSPGPLSHAGS(-1)IGCNKQLFSPSLASSTFSGS
(Pt)CNS     CGEMLGCCQTSTLTLLSPGRPSHAGS(-1)IGCNSTLFSPSLASSIFSGS
(Pt)LN/SP   LRDEMPGGCQTSTLRLLSLGRPSHAGS(-1)IGCNRLLFSPSLASSIFSAS

SF2         TGTSLKHHPKVSGYLIPGPGV
YU2         TGTSLKHHPKVSGIILVP-PGV
JR-FL       TGTSLKHHPKVNGNLIPGPGV
(Pt)CNS     TGTSLKHHPKVSGYLVPGPGV
(Pt)LN/SP   TGTSLKHHPKVSGYLIPGPGV
```

(-1/+1 ribosomal frameshift(s))
```
SF2         MQHLRARHSPVPPRPRLPGKSPAESPL (-1)VESSMSAVFVVLRMQLSG
YU2         MQHLRARHSPVPPRPRFPGKSPAESPL (-1)VESSRSSVLVVLRMQLSG
JR-FL       MQHLRARHSPVPPRPRLPGKSPVESPL (-1)VESSMSAVLVVLRMQLSG
(Pt)CNS     MQHLRARHSPVPPRPHLPGKSPAESPL (-1)VESSMSSVLVVLRMQLSG
(Pt)LN/SP   MQHLRARHSPVPPSPRLPGKSPAESPL(-1)VESS( )MSAVLVVVRMQLSG
                                             (VSAVS)

IblrevINRold**                              MSAVFVVLRMQLSG
HXB2(TCLA) MQDLRARHSPVPPRPRLPGKSPAESPL(-1) VASSMSAVLEVLRMQLSG SF2          HVMKC(+1) SLLSNLHTNTSFSASSIPCR  LIGCNKLLFSPSLASSTFSGS
YU2          HVMKC(+1) RRLSNLHSNPSLSGSSIPCW  LIGCNKQLFSPALASSIFSGS
JR-FL        HVMKC(+1) SLLSNLHSNTSFSGSSIPCR  LIGCNKQLFSPSLASSTFSGS
(Pt)CNS      PVVKC (+1) RVLSNFHTNTSLSGSSIPCR LIGCNNTLFSPSLASSIFSGS
(Pt)LN/SP    YVMKCQAAVKPPLLRLLSLGPPSHAGS(-1)IGCNRLLFSPSLASSTFSAS
IblrevINRold HVTKC (+1) RRLSNFHTNTSPSGSSIPCW LIGCNKLFFSPYLASSTCSGS
HXB2         HVMKC(+1) RRLSNLHSNTSLSGSSIPCR  LTGCNKLVFSPLLASSNFSGS SF2          TGTSLKHHPKVSGYLIPGPGV
YU2          TGTSLKHHPKVSGIILVP-PGV
JR-FL        TGTSLKHHPKVNGNLIPGPGV
(Pt)CNS      TGTSLKHHPKVSGYLVPGPGV
(Pt)LN/SP    TGTSLKHHPKVSGYLIPGPGV
IblrevINRold TGTNLKHHPLVSGYLIPGPGV
HXB2         TGTSL
```

FIG. 8

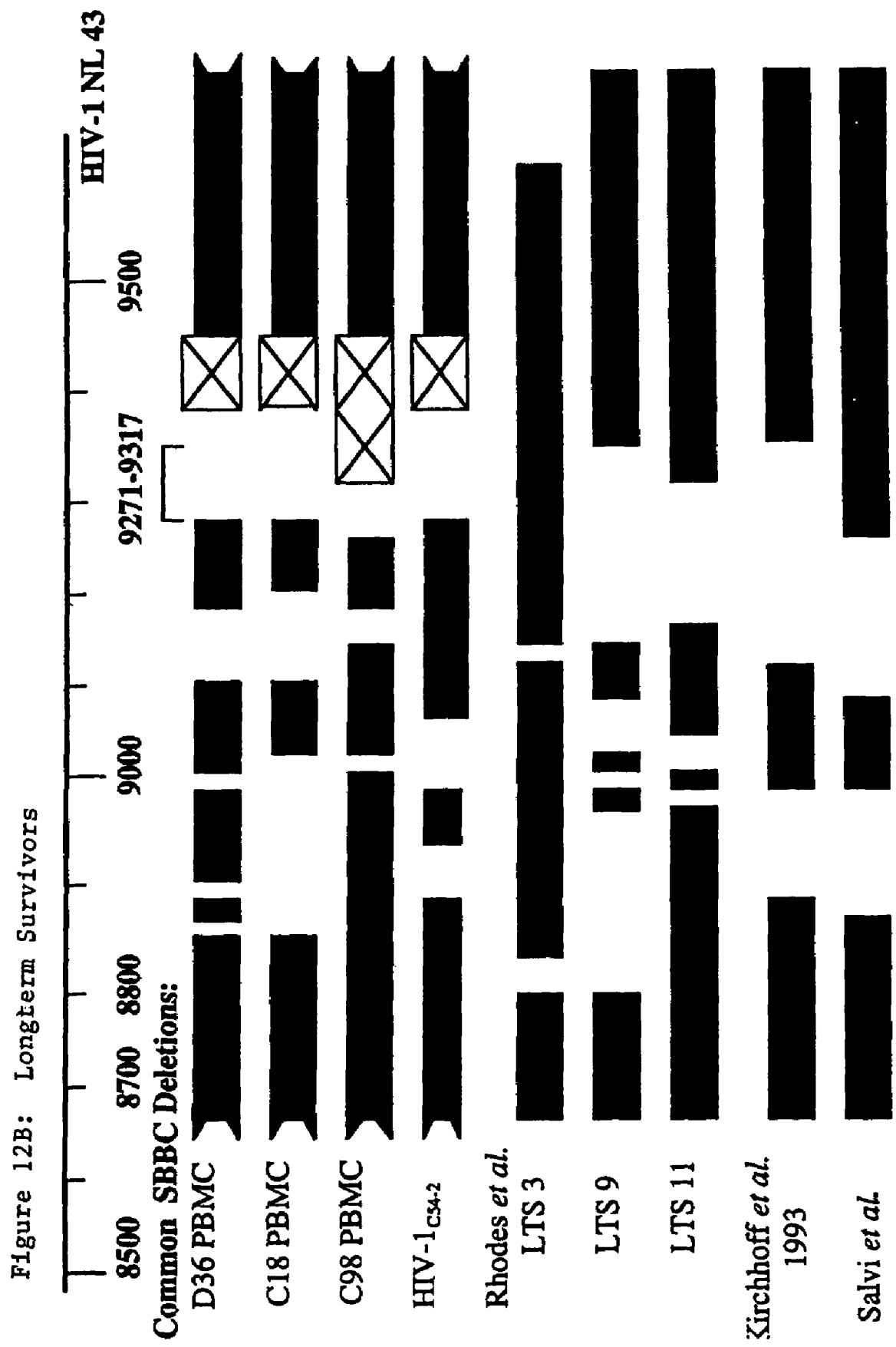
Figure 12B: Longterm Survivors

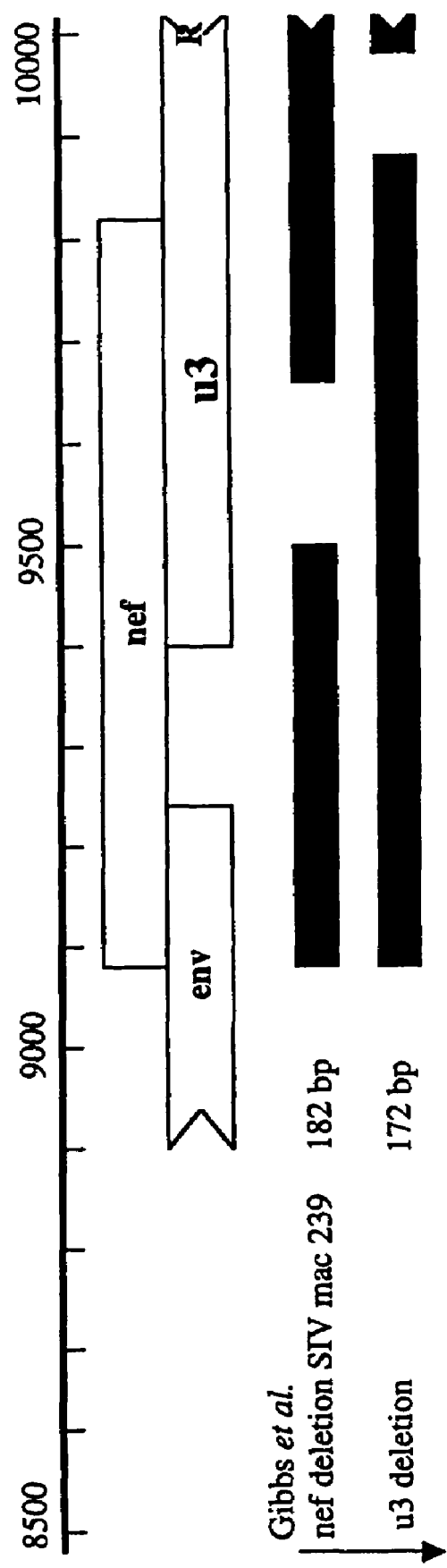
Figure 12C: SIV mac 239 (Regier and Desrosiers)

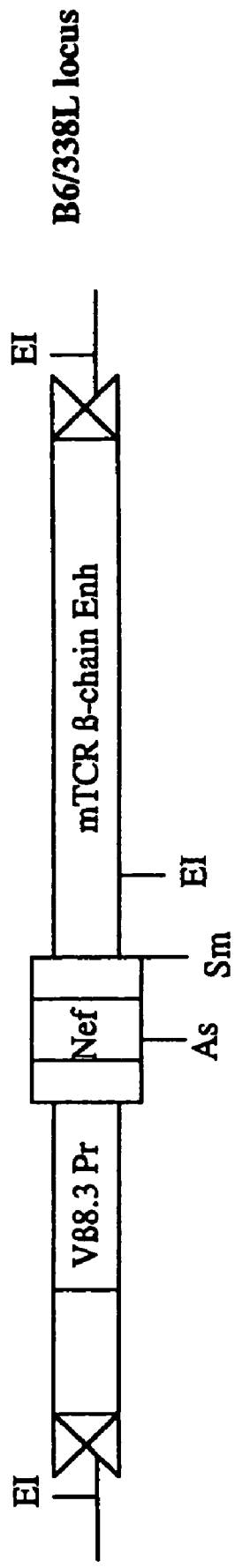
Figure 12D: Mouse Transgene Associated with Severe Immunodeficiency (Lindemann et al.)

HIV ANTISENSE PROTEINS

This application is a divisional of application Ser. No. 10/135,545, filed on Apr. 30, 2002 now abandoned, which is a continuation-in-part of application Ser. No. 09/249,542, filed on Feb. 12, 1999, now U.S. Pat. No. 6,392,029 which claims priority of provisional application No. 60/074,640 filed on Feb. 13, 1998, and is also a continuation-in-part of application Ser. No. 08/853,703, filed on May 9, 1997, now U.S. Pat. No. 5,919,677, the disclosures of which are incorporated herein by reference.

This invention was made with government support under grants R29AI38114-01 and R21AI46960 awarded by the National Institutes of Health. The government has certain rights in the invention.

BACKGROUND OF THE INVENTION

1. Field of the Invention

The present invention relates to a novel gene of HIV, the virus causing AIDS, which encodes a protein having an amino acid sequence that is closely related to the chemokine family of proteins. More particularly, the invention relates to a novel HIV protein that may be a cofactor for binding to the chemokine receptor on human cells during the entry phase of infection.

2. Description of the Background and Related Art

1. The Chemokine Receptors as Coreceptor for HIV Infection

Efficient entry of HIV into target cells is dependent upon a high affinity binding of the viral envelope glycoprotein, gp120, to the amino terminal domain of CD4, a protein expressed on the surface of the domain of CD4, a protein expressed on the surface of the target cell. While CD4 is the primary virus receptor, CD4 alone is not sufficient for virus entry. Chemokine receptors have been identified as the coreceptors involved in the entry of HIV into target cells.

Macrophage-tropic ("M-tropic") HIV-1 use the β-chemokine receptor CCR5, and less often receptor CCR3, as their coreceptor (Choe et al., 1996, Cell 85:1135-1148; Dragic et al., 1996, Nature 381:667-673; Deng et al., 1996, Nature 381:661-666). Mutations in CCR5 appears to confer resistance to infection by M-tropic HIV-1 viruses in vivo and in vitro (Samson et al., 1996, Nature 382:722-725). T-tropic (lymphotropic strains which grow in cells including transformed T cell lines) HIV generally use the α-chemokine receptor CXCR4 (also known as fusin, SDF-1 chemokine receptor, LESTR; Feng et al., 1996, Science 272:872-877). CXCR4 also can function as the primary receptor for HIV-2 entry and infection of human CD4-negative cells (Endres et al., 1996, Cell 87:745-756). Dual-tropic primary HIV-1 isolates, that can infect both macrophages and T cells, can use either CCR5 or CXCR4 (and possibly CCR3 or CCR-2b) as the coreceptor involved in virus entry (Doranz et al., 1996, Cell 85:1149-1158). There is evidence suggesting that the structure of the gp120 V3 loop influences the ability of HIV to bind the chemokine receptors on the target cell (Choe et al., 1996, supra; Doranz et al., 1996, supra).

2. HIV Secondary Structures

Single stranded RNA form localized regions of secondary structures such as hairpin loops and pseudoknot structures (Schimm, 1989, Cell, 58-9-12). A RNA population was isolated that bound to HIV reverse transcriptase and that has a pseudoknot consensus (Tuerk et al., 1992, Proc. Natl. Acad. Sci., USA. 59:6988-6992). Pseudoknots are structures in which there is an intramolecular base pairing of the "loop" sequence of an RNA hairpin to sequences either 5' or 3' to that hairpin. Pseudoknots are generally formed in nucleic acid sequences of about 30 to 60 nucleotides. Such intramolecular base pairing is key to the translation of RNA since the presence of pseudoknots can lead to frameshifting either in the 5' or the 3' direction (generally designated as −1 or +1) or for allowing read-through. Translational frameshifting allows the expression of alternative translational products in a predictable stoichiometry (ala retroviral or HIV gag-pol fusion peptide); to allow the expression of alternative enzymatic activities; or as a mechanisms for autogenous control (see Farabaugh, 1996, Microbiol Rev. 104).

3. Chemokines

Chemokines are a superfamily of soluble proteins that are involved in immune regulation and in inflammatory processes (such as leukocyte recruitment). Generally, chemokines range in size from about 70 to about 100 amino acids, and in molecular size from about 8 kilodaltons (kD) to about 11 kD. Chemokine like proteins have also been described that are membrane bound (Pan et a., 1997, Nature, 387:611). The chemokines share related primary structure, particularly with a conserved motif of four cysteine residues. Early classification of chemokines was based on whether the first two cysteines are adjacent to each other ("CC chemokines"), or are separated by one amino acid ("CXC chemokines"). More recently, chemokines with a single "C" motif (for example lymphotactin) and "CXXXC" motif (for example, neurotactin) have been described. The α-chemokine receptor CXCR4 has been identified as a coreceptor required for HIV entry. The only known natural ligand for CXCR4 has been identified as the CXC chemokine SDF-1. SDF-1 has been shown to inhibit infection of CXCR4 and CD4 expressing cells by T-tropic HIV-1 strains (Oberlin et al., 1996, Nature 382:833-835). Thus, modified versions of chemokines are being tested to determine whether they may be used to block chemokine receptors from binding by HIV.

Kaposi's sarcoma is an AIDS-related malignancy. The Kaposi's sarcoma-associated herpesvirus (KHSV, human herpesvirus 8) has been shown to encode a chemokine receptor ("GPCR") that is analogous in sequence and chemokine specificity to CXCR2 (Arvantikas et al., 1997, Nature 385: 347-349). This is not the only instance in which a virus has apparently pirated a cellular gene encoding either a chemokine or a chemokine receptor. KSHV and *Molluscum* contagiosum have open reading frames that encode CC chemokines; and Herpesvirus Saimiri, human cytomegalovirus, KSHV, Equine herpesvirus-2, Swine pox virus, and capripox virus have open reading frames encoding chemokine receptors (Murphy, 1997, Nature 385:296-299; Neote et al., 1993, Cell 72:415-425).

4. HIV Proteins

The HIV genome is known to contain 8 open reading frames on the minus strand of the double-stranded DNA intermediate. From the HIV double-stranded intermediate, and from the HIV promoter located in the 5' LTR, mRNAs of plus strand polarity are transcribed from the minus strand DNA template (see Definitions section herein). Depending on the processing of the transcript, the mRNA may then be translated into one or more viral-proteins including Gag, Pol, Vif, Tat, Vpu, Vpr, Rev, Env, and Nef. Additionally, ribosomal frameshifting is employed to enable gag pol protein. Effective transcription from the 5'LTR HIV promoter is dependent on the presence of Tat for transcriptional activation that dramatically increases the levels of viral mRNAs. A possibility was raised that the plus strand of the viral DNA contains a long open reading frame (ORF), located in the region of the genome complementary to the env gene sequence, that may encode a viral protein of 190 amino acids and a molecular mass of 20 kilodaltons (Miller, 1988, Science 239:1420-1422). However, it is not apparent whether this possibility was confirmed, such as by the demonstration of the putative protein or its respective mRNA. In fact, it is noted in the publication that it is possible that the ORF does not represent a true gene sequence. The possibility that bidirectional transcription occurs in HIV was further evaluated by Michael et al. (1994, J. Virol. 979-87).

Accordingly, there has been and continues to be a long-felt need for the identification of novel HIV proteins which play a role in AIDS pathogenesis, and thus may be important targets of therapeutic intervention.

SUMMARY OF THE INVENTION

The present invention relates to the discovery of a novel gene comprising open reading frames (ORFs) in the plus strand of the proviral DNA, and located in the HIV LTR. The plus strand of the proviral DNA is the DNA strand that comprises a sequence identical to the plus strand RNA constituting the HIV genome (with each uracil in the RNA substituted by thymidine in the DNA). The proviral plus strand therefore serves as template for messenger RNA that is complementary to the plus strand HIV genomic RNA. Thus, the gene of the present invention is termed an "HIV antisense gene" because the RNA transcript produced from this gene is complementary to the RNA plus stranded genome of the HIV. An antisense initiator element initiates production by RNA polymerase of antisense RNA, which are RNA transcripts of negative strand polarity utilizing the plus strand DNA as a template. Thus, using this mechanism, the novel HIV gene is transcribed by the cellular transcriptional apparatus. The gene also encodes a protein that is related to, and has a structural motif resembling that of a chemokine. More particularly, the protein has similarity to the chemokine family of proteins. Theme objects and further features and advantages of the invention will be better understood from the description of the preferred embodiments when considered in relation to the figures.

BRIEF DESCRIPTION OF THE FIGURES

FIG. 1a is a schematic representation of the HIV genome illustrating the position of the HIV chemokine-like gene in relation to other HIV genes and regulatory sequences (Meyers et al., 1995, A compilation and analysis of nucleic acid and amino acid sequences, Los Alamos National Laboratory, Los Alamos, N. Mex.).

FIG. 1b is a schematic representation of the LTR region of HIV illustrating the position of antisense RNA initiation.

FIG. 7 is a schematic representation illustrating sequence analysis and alignment between amino acids of an HIV chemokine and other chemokines.

FIG. 8 is a schematic representation illustrating sequence alignment between amino acids of HIV chemokines from various cell lines and patient HIV isolates.

DETAILED DESCRIPTION OF THE INVENTION

Definitions

Figure 2A:
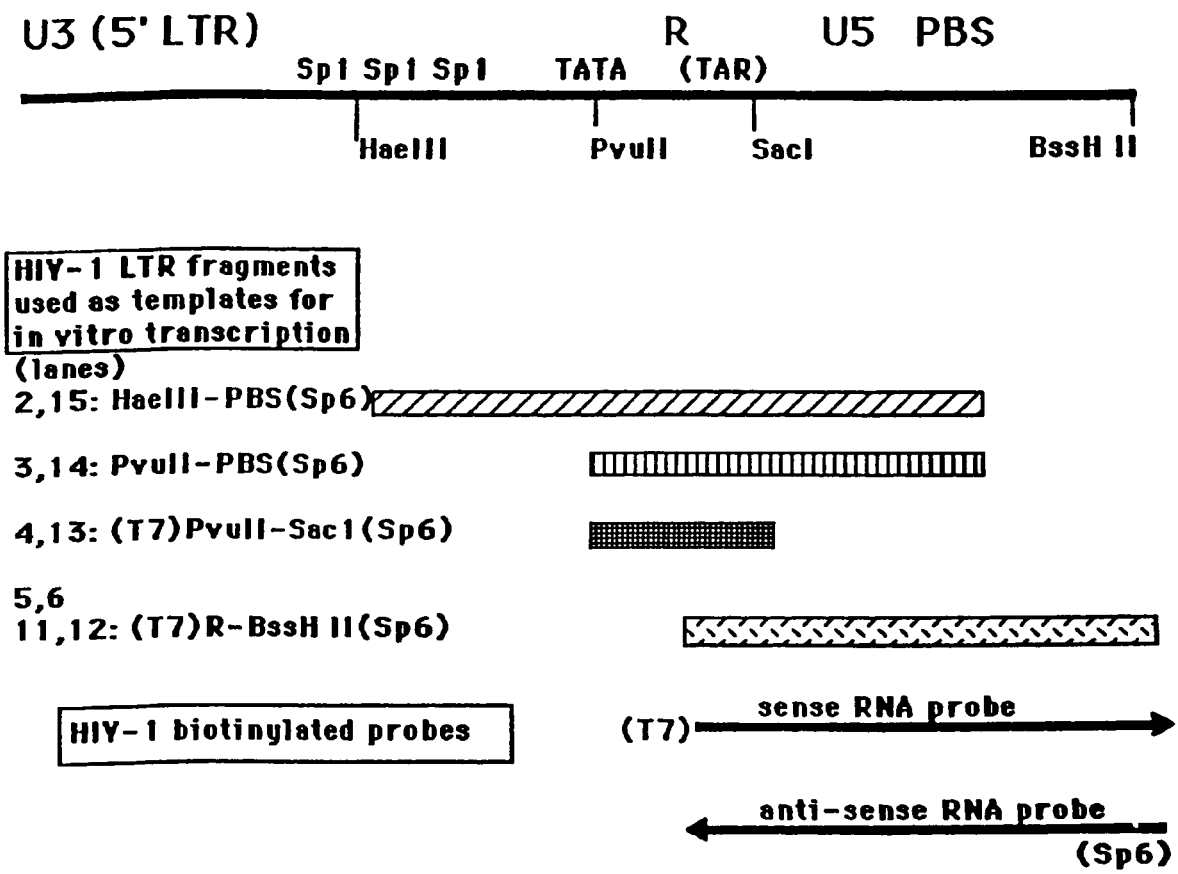
FIGS. 2a and 2b are schematic illustrations of the 5' LTR of HIV and the templates derived therefrom for in vitro transcriptions.

By the term "operably linked" is meant, for the purposes of the specification and claims to refer to the chemical fusion (enzymatic restriction with subsequent ligation) or synthesis of heterologous DNA with a nucleotide sequence that encodes an HIV chemokine such that the resultant recombinant DNA molecule is formed in a proper orientation and reading frame for the nucleotide sequence to be transcribed into functional RNA. In the construction of the recombinant DNA molecule, it is generally preferred to position a promoter at a distance upstream from the initial codon of the nucleotide sequence that is approximately the same as the distance in its natural setting (e.g., as in the HIV genome). However, as known in the art, some variation in the distance can be accommodated without loss of promoter function. Likewise, it is generally preferred to position an enhancer element at a distance upstream from the promoter, or incorporated into the promoter sequences as a promoter element, or located between the promoter and the DNA molecule to be expressed. However, as known in the art, some variation in the placement can be accommodated without loss of the enhancer element’s function.

By the term “expression vector” is meant, for the purposes of the specification and claims to refer to a DNA molecule which is operably linked to a nucleotide sequence that encodes an HIV chemokine such that the production of the HIV chemokine is effected in a suitable host. The vector may include, but is not limited to, a plasmid, phage, viral vectors, viral-like vectors, or a potential genomic insert.

By the terms “variant of the nucleotide sequence” or “variant of the gene” or “variant sequence” are meant, for the purposes of the specification and claims to refer to a nucleotide sequence that shares substantial identity (an identity of greater than about 70%, not taking third base degeneracy into account) with the gene encoding HIV chemokine. Such a sequence comparison can be performed using existing software known to those skilled in the art. Variants can be natural variants or variants produced by synthetic or mutagenic means for modifying the disclosed nucleotide sequences. With respect to such variations, and as appreciated by those skilled in the art, because of third base degeneracy, almost every amino acid can be represented by more than one triplet codon in a coding nucleotide sequence. Thus, a variant sequence can be modified slightly in sequence (e.g., substitution of a nucleotide in a triplet codon), and yet still encode its respective gene product of the same amino acid sequence as encoded by the disclosed nucleotide sequences. Further, variant sequences may have minor base pair changes which may result in variation (conservative substitution) in the amino acid sequence encoded. Such conservative substitutions are not expected to substantially alter the biologic activity of the gene product. A conservative substitution or modification of one or more amino acids are such that the tertiary configuration of the protein is substantially unchanged. "Conservative substitutions" is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine. A variant sequence may contain a modification, being defined functionally as resulting in a deletion or addition or substitution of one or more amino acids which does not impart a substantial change in the HIV chemokine that it encodes; i.e., if the encoded HIV chemokine substantially retains the activity of being a cofactor in binding to a chemokine receptor. Such an encoded HIV chemokine may be referred to as a modified variant of HIV chemokine. Methods for synthetically producing such variant sequences are known to those skilled in the art (see, e.g. U.S. Pat. Nos. 5,403,737 and 5,275,945).

By the term "similarity" are meant, for the purposes of the specification and claims to refer to amino acids that are not identical, but similar (amino acids having substantially the same charge, size, hydrophilicity, and/or aromaticity) between two amino acid sequences as determined by sequence comparisons performed using algorithms known to those skilled in the art.

By the term "identity" are meant, for the purposes of the specification and claims to refer to amino acid positions that are identical between two amino acid sequences as determined by sequence comparisons performed using algorithms known to those skilled in the art.

By the term "individual" is meant, for the purposes of the specification and claims to refer to any mammal, especially humans.

By the term "regulatory element" is meant, for the purposes of the specification and claims to refer to an promoter element motif which functions to facilitate binding or recruitment of RNA polymerase or transcription factors in the initiation, activity, and efficiency, of transcription. Eukaryotic regulatory elements include, but are not limited to an antisense initiator, an ATF site, TATA box, a TATA-like box (e.g., TTTAA, TTTAAA, TAT, TAATA), a CAAT box, a CAAT-like box (e.g., CTAATC), upstream stimulatory factor (USF), upstream sequence element (USE), and binding sites for transcription factors (e.g., AP-2, SP1, CRE, PEA-3, NF-IL6, NF-Kβ etc.).

By the terms "HIV Chemokine-like Protein" or "HIV-chemokine" or "Hap" is meant, for the purposes of the specification and claims, to refer to a protein having the following distinguishing and functional characteristics:

(a) a protein encoded by an HIV antisense open reading frame which encodes domains having at least 10% homology to amino acid sequences of chemokines.

(b) is expressed by strains of HIV in at least one phase of virus replication, and is encoded by an open reading frame in the plus strand of the proviral dsDNA, and located in the LTR region.

The term, "Chemokines" includes, but is not limited to, CC chemokines, CXC chemokines, single C motif chemokines (e.g. lymphotactin), CXXXC chemokines (e.g. neurotactin). The chemokine may be membrane bound or secreted.

By the terms "isolated and purified" and "substantially free from other proteins" is meant, for the purposes of the specification and claims, to refer to an HIV chemokine protein preparation that appears to be at least approximately 80% pure, and may be up to approximately 99% pure, as, for example, determined by gel electrophoresis, or liquid chromatography.

By the term "target cell" is meant, for the purposes of the specification and claims, to refer to a human cell which is infectable by HIV including, but not limited to, CD4+ cells bearing chemokine receptors, and CD4-negative cells bearing chemokine receptors; and also refers to human or other mammalian cells bearing chemokine receptors which receptors can bind to soluble HIV chemokine.

The present invention is directed to a gene, represented by an open reading frame in the plus strand of the proviral dsDNA of HIV, which encodes a protein designated "HIV chemokine" or "Hap". One reason that this gene and its gene products remained unknown until the present invention was the lack of discovery and characterization of the antisense initiator element which allows initiation by RNA polymerases of RNA transcripts of negative strand polarity utilizing the plus strand of the HIV dsDNA LTR pro-viral intermediate as a template (U.S. patent application Ser. No. 08/853,703, now U.S. Pat. No. 5,919,677).

It is now established that chemokine receptors act as coreceptors, with CD4, necessary for HIV to enter a target cell. Additionally, certain chemokine receptors (e.g., CXCR4) may act as the primary viral receptor, in the absence of CD4, necessary for HIV to enter a CD4-negative target cell (Endres et al., 1996, Cell 87:745-756). Thus, HIV cofactors that act on their own or in conjunction with gp120 in the binding to the target cell's chemokine receptor represent components critical in HIV pathogenesis. Chemokines, including RANTES, MIP-1α, and MIP-1β, have been shown to bind to the CCR5 chemokine receptor and inhibit infection by HIV. SDF-1 has been shown to bind CXCR4 and inhibit infection by T-tropic HIV-1 strains. Other chemokines, that bind to one or more chemokine receptors that act as either coreceptors or primary viral receptors, are being sought as drug candidates in their natural state. Additionally, such chemokines are being modified to produce versions which may bind to the chemokine receptor, but not act as an agonist (Science 275:1261-1264, 1997; Simmons et al., 1997 Science 276:276-279).

The unexpected finding that HIV encodes its own chemokine-like protein, and that the chemokine-like protein may act as a cofactor with gp120 in the binding to and entry of HIV to a target cell, is an important consideration for therapeutic intervention. Thus, the peptides derived from the HIV chemokine gene or variants or modified versions of the HIV chemokine may be used to block entry of target cells during various phases of HIV infection and AIDS. Additionally, chemokine receptors may provide a method by which the HIV chemokine may be isolated and purified from HIV. Alternatively, one or more monoclonal or polyclonal antibodies having binding affinity and specificity for the HIV chemokine may be used as affinity molecules immobilized to an affinity matrix for isolation and purification of the HIV chemokine.

Further, the unexpected finding that HIV encodes its own chemokine-like protein provides evidence that the HIV chemokine is involved in at least one of the mechanisms of AIDS pathogenesis. In that regard, there may be biological properties of the HIV chemokine in addition to that of acting as a cofactor with gp120 or an independent ligand for binding to a target cell, in the binding of HIV to and entry of HIV into a target cell. For example, chemokines in general, and more specifically β-chemokines such as MIP-1α and MIP-1β, can be potent chemoattractants for both monocytes and specific subpopulations of lymphocytes (Schmidtmayerova et al., 1996, Proc. Natl. Acad. Sci. USA 93:700-704). Thus, both human β-chemokine expression induced in HIV infection, and the HIV chemokine-like protein, may function to recruit uninfected T cells and monocytes to sites of active viral replication or inflammation.

Such recruitment of uninfected T cells which are CD4+ to sites of active viral replication, such as in the lymph node, may play a role in the decline of CD4+ T cells observed in the progression of AIDS. Such recruitment of mononuclear phagocytes to sites of active viral replication, such as in the brain, with subsequent activation of the mononuclear phagocytes to produce cytokines and NO (nitric oxide), may play a role in tissue pathology such as the neuropathogenesis observed in AIDS (Shapshak et al., 1995, Adv. Exp. Med. Biol. 373:225-238; Bukrinsky et al., 1995, J. Exp. Med. 181: 735-745; Achim and Wiley, 1996, Curr. Opin. Neurol. 9:221-225). Additionally, through genetic variation, HIV may be able to control HIV chemokine expression depending on the tissue type in which it is adapting. In that regard, it is noted that HIV present in spinal cord and dorsal root ganglion harbour an LTR population genetically distinct in sequence from that present in other organs including lymph node, spleen, lung, and peripheral blood (Ait-Khaled et al., 1995, AIDS 9:675-683). Such variation in the LTR sequence can include variations in the sequence of the HIV antisense initiator element, and thus the expression of the HIV chemokine from the antisense initiator element. The heterogeneity of the HIV LTR isolated in various tissues may reflect the predominant collection of mutations in the cells infected in those tissues. Thus, an important consideration in treating or preventing AIDS pathogenesis in certain tissues may be to inhibit the HIV chemokine from recruiting lymphocytes and mononuclear phagocytes to sites of active viral replication. Alternatively, the heterogeneity of the HIV LTR may be part of the mechanism whereby the HIV chemokine acquires the capacity to ligand with a chemokine receptor expressed in a specific tissue as illustrated in FIG. 8 (+/−ribosomal frameshifting). It should be noted that a CNS derived HIV chemokine contains "CC" motif, whereas a LN/spleen contains "XC" chemokine.

Kaposi's sarcoma is a malignancy that is rare in individuals uninfected with HIV, but frequent in (up to 20 percent of) homosexuals with AIDS. Kaposi's sarcoma-associated herpesvirus (KSHV) is thought to be the virus that is the etiologic cofactor of Kaposi's sarcoma in AIDS patients (Kedes et al., 1996, Nat. Med. 2:918-924; Arvanitakis et al., 1997, Nature 385:347-349). Recently, discovered was a chemokine receptor produced by KSHV ("KSHV GPCR") which may act as a cofactor in AIDS-related malignancies including Kaposi's sarcoma and primary effusion lymphoma (PEL) (Arvanitakis et al., 1997, supra). However, the expression of this chemokine receptor on an KSHV-infected cell is not sufficient to lead to altered growth or neoplastic transformation. Rather, signaling of cell-KSHV GPCR is required by a cofactor produced during AIDS pathogenesis before altered growth or neoplastic transformation is initiated. Epidemiologic data supports this scenario, since KSHV appears to be sexually transmitted but malignancy primarily occurs only in AIDS patients; i.e., a sexually transmitted agent leading to AIDS-related malignancy rather than just a sexually transmitted agent leading to malignancy. While chemokines of the CXC class or CC class have been shown to bind to KSHV GPCR (Arvanitakis et al., 1997, supra), a logical cofactor that is HIV-related and thus explains the association between AIDS and malignancies including Kaposi's sarcoma and PEL is the HIV chemokine. That is, the HIV chemokine and KSHV GPCR are cofactors that interact to initiate cell signals leading to altered growth or neoplastic transformation in KSHV-infected cells. To interact with the KSHV GPCR which is membrane bound in the KSHV-infected cells, the HIV chemokine may either be soluble (e.g., secreted from HIV-infected cells), or a component of a viral particle or HIV infected cell membrane (e.g., interacting by itself as a membrane bound receptor or in conjunction with gp120).

Alternatively, the HIV chemokine and variants expressed in various tissues or cell lines may represent an ideal vaccine candidate for AIDS prevention in as much as the isolated and purified HIV chemokine (and variants) could be administered as vaccines to stimulate the human individual's intrinsic immune response to a "foreign" HIV chemokine without presumably interfering with human intrinsic chemokines necessary for recruitment of inflammatory responses.

Because the HIV chemokine appears to play an important role for AIDS pathogenesis in vivo, one therapeutic approach is to consider using the HIV chemokine as an immunogen in a vaccine (including multivalent) formulation against disease caused by HIV infection. Thus, isolated and purified HIV chemokine, or peptides made by enzymatically cleaving HIV chemokine or synthesis using the amino acid sequence of HIV chemokine as a reference, may be used as immunogens in various vaccine formulations to prevent HIV entry into target cells, and/or in the prevention of tissue pathology in certain tissues caused by the HIV chemokine's recruitment of lymphocytes and mononuclear phagocytes to sites of active viral replication, and/or to prevent HIV chemokine from interacting with potential chemokine receptors such as KSHV-GPCR.

More specifically, the resultant anti-HIV chemokine-antibodies may function to clear the tissue of chemoattractant HIV chemokine, and/or as "neutralizing" antibodies to block HIV chemokine from acting as a cofactor in binding to chemokine receptors such as for the entry of HIV into target cells or such as expressed by a KSHV-infected cell. Additionally, according to the present invention, the HIV chemokine, or peptides derived therefrom, may be used to generate HIV chemokine-specific antisera (human polyclonal antibody, or human-compatible monoclonal antibody including chimeric antibody) useful for passive immunization in HIV-infected individuals to clear the tissue of chemoattractant HIV chemokine, and/or as "neutralizing" antibodies to block HIV chemokine from acting as a cofactor in binding to chemokine receptors such as for the entry of HIV into target cells or such as expressed by a KSHV-infected cell.

Alternatively, peptides; modified peptides (collectively referred to as "peptides") or modified variants of HIV chemokine derived from the amino acid sequence of the HIV chemokine may be used as a therapeutic agent. For example, such a peptide (e.g., 7 to 20 amino acids) or modified variant of HIV chemokine may be synthesized so as to minimize inducing an immune response, or have reduced or lack function as a chemoattractant, but retain the receptor binding function of either an antagonist or an agonist. As an antagonist, the peptide or modified variant of HIV chemokine would bind to at least one type of chemokine receptor which acts as a coreceptor or primary viral receptor for HIV entry or associated with AIDS pathogenesis, thereby blocking subsequent interaction of HIV with a target cell uninfected by HIV. In a preferred embodiment, the antagonist would be able to bind to and block more than one type of such chemokine receptor (e.g., more than one of CCR5, CXCR4, CCR3, CCR-2b, KSHV GPCR, or any combination thereof). As an agonist, the peptide or modified variant of HIV chemokine would bind to at least one type of chemokine receptor which acts as a coreceptor or primary viral receptor for HIV entry or associated with AIDS pathogenesis, thereby blocking subsequent interaction of HIV with a target cell uninfected by HIV. Additionally, the binding of the agonist to the target cell chemokine receptor would trigger the receptor to signal the cell to down-regulate the expression of the chemokine receptor, the same signal generated by binding of a chemokine to its receptor (see, e.g., chemokine agonist in receptor binding—Hunter et al., 1995, Blood 86:4400-4408). In a preferred embodiment, the agonist would be able to bind to and block more than one type of such chemokine receptor (e.g., more than one of CCR5, CXCR4, CCR3 or CCR-2b, or any combination thereof). In using such a peptide or modified variant of HIV chemokine, it is noted that human testing of a MIP-1α variant (BB-10010) in cancer and HIV studies seems to be well tolerated and not inflammatory (Lord et al., 1996, Br. J. Cancer 74:1017-1022).

As reviewed above, HIV chemokine production may be modulated, depending upon the tissue type to which it has adapted. Thus, isolated and purified HIV chemokine, or peptides derived therefrom, may be used as an antigen in diagnostic immunoassays directed to detection of HIV infection for staging or to monitor response to anti-viral therapy by measuring the body fluid (e.g., serum, cerebral spinal fluid (CSF), or urine) titer of any anti-HIV chemokine antibody that may be present in the HIV-infected individual. Also, isolated and purified HIV chemokine, or peptides derived therefrom, may be used to generate HIV chemokine-specific antibody which may be useful as reagents for diagnostic assays directed to detecting the presence of HIV chemokine in clinical specimens. Measurements of chemokine levels for chemokines that are cell differentiation-associated (Vinante et al., 1996, Haematologica 81:195-200), or for monitoring efficacy of therapy (Segawa et al., 1996, Intern. Med. 35:155-158) have been described previously. Alternatively, reverse transcription-nucleic acid amplification reactions with primers specific for amplifying all or a portion of the HIV chemokine sequence may be utilized to detect the presence of the HIV chemokine sequences in clinical specimens for staging or to monitor response to anti-viral therapy. Similar methods of nucleic acid amplification have been described previously for determining cell type-specific heterogeneity of the HIV-1 V3 loop in HIV-infected individuals (Yamashita et al., 1994, Virology 204:170-179); or to monitor the LTR variation (Ait-Khaled et al., 1995, supra).

For purposes of the description, the methods and compounds of the present invention will be illustrated in the following examples.

Example 1

A gene encoding an HIV chemokine according to the present invention can be obtained by isolating the HIV dsDNA intermediate from an HIV-infected cell, or may be synthesized in vitro by reverse transcriptase-nucleic acid amplification from the antisense mRNA originating from the HIV antisense initiator, HIVaINR. FIG. 1 illustrates the position of the HIV chemokine gene in relation to other HIV genes and regulatory elements.

Alternatively, since the HIV chemokine gene is coded for by the plus strand of the HIV, which is complimentary to the minus strand, the sequence of a given strain of HIV chemokine gene can be deduced from the known LTR region sequences of HIV strains available in gene databanks (see also Human retroviruses and AIDS 1995, a compilation and analysis of nucleic acid and amino acid sequences. Ed. G. Mayers, Los Alamos national Laboratory). To further illustrate this embodiment, the nucleotide sequence of the antisense gene encoding the HIV chemokine of lbl revINRold was deduced (SEQ ID NO:1) utilizing the nucleotide sequence of the HIV minus strand. This sequence termed as "HIV chemokine gene" has an antisense initiator, aINR, at position 60-68 (SEQ ID NO:1). Tha aINR has the consensus 5' Py Py A N T/A Py Py 3' as disclosed in our application Ser. No. 08/853,703, now U.S. Pat. No. 5,919,677. A TATA box is present about 42 nucleotides downstream from the site of antisense initiation and in the opposite orientation at nucleotides 110-114. There is also an ATF consensus site upstream of the antisense gene. The open reading frame encodes a protein of 81 amino acids (SEQ ID NO:2). The production of this protein requires a frameshift at the nucleotide at position 263 of SEQ ID NO:1. The frameshifting is potentiated by the formation of pseudoknot structures in the RNA. The lbl revINRold sequence is derived from pNLgag (Adachi et al., J. Virology, 59:284-291) which has a mutation following the first start codon of HIV chemokine at nucleotide 114 such that a stop codon immediately follows. Therefore, the second start site at nucleotide 206 is utilized. However, most other HIV strains actually have the first start codon available and potentially viable, which would entail sets of ribosomal frameshifts and code for larger proteins.

Figure 9:
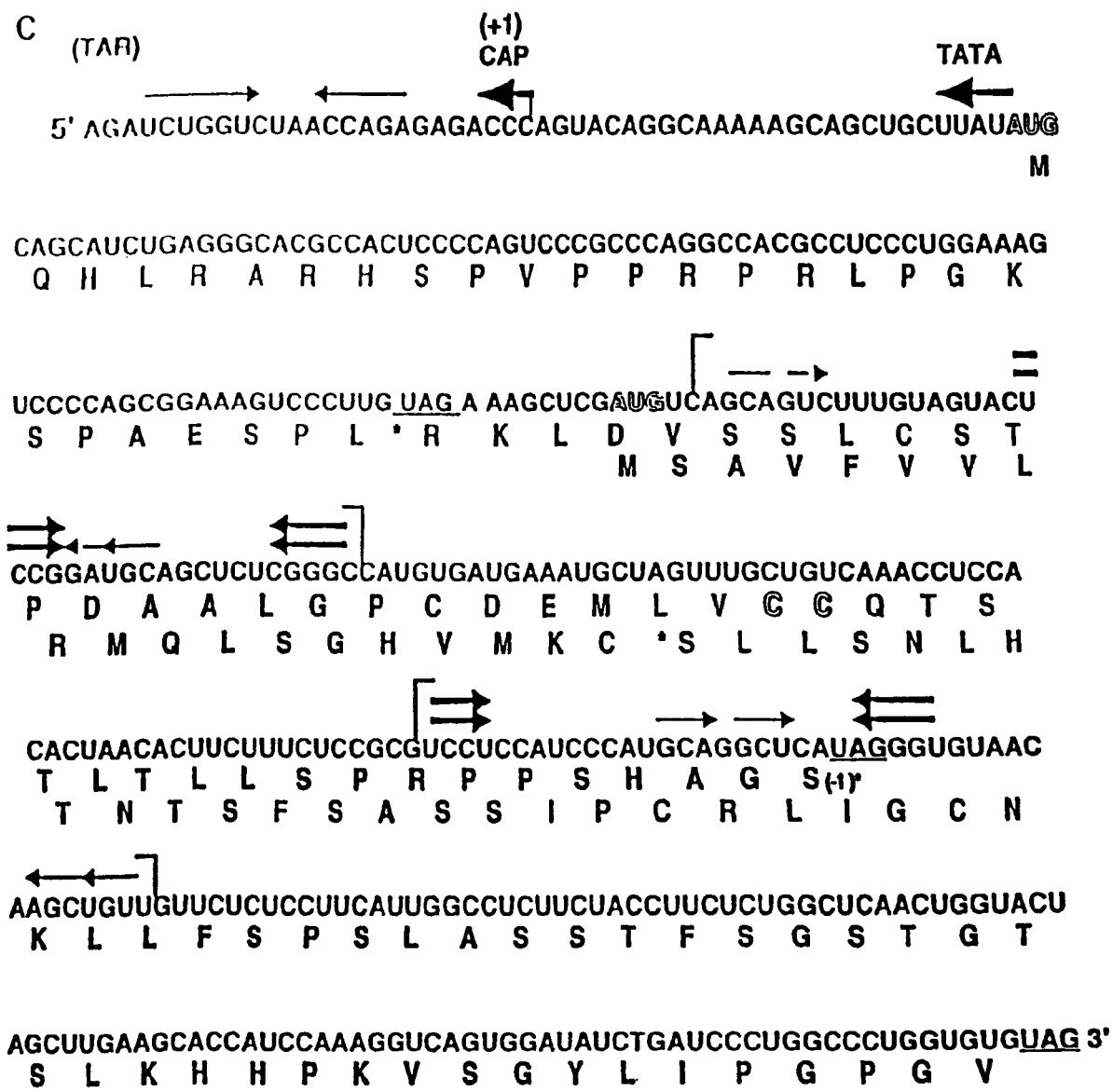
FIG. 9 is a schematic representation illustrating the sequence and presence of pseudoknots.
Figure 10A:
FIG. 10A-F are photomicrographic representations of the effect of transfection of a HeLa cell line with constructs containing the HIV LTR region.
Figure 10B:
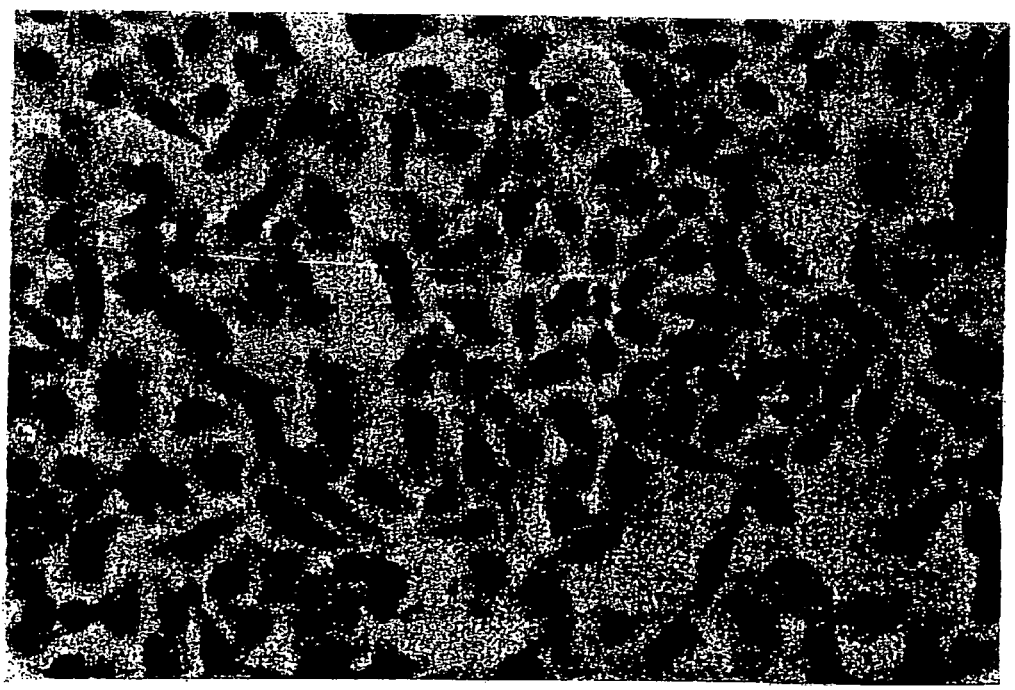
Figure 10C:
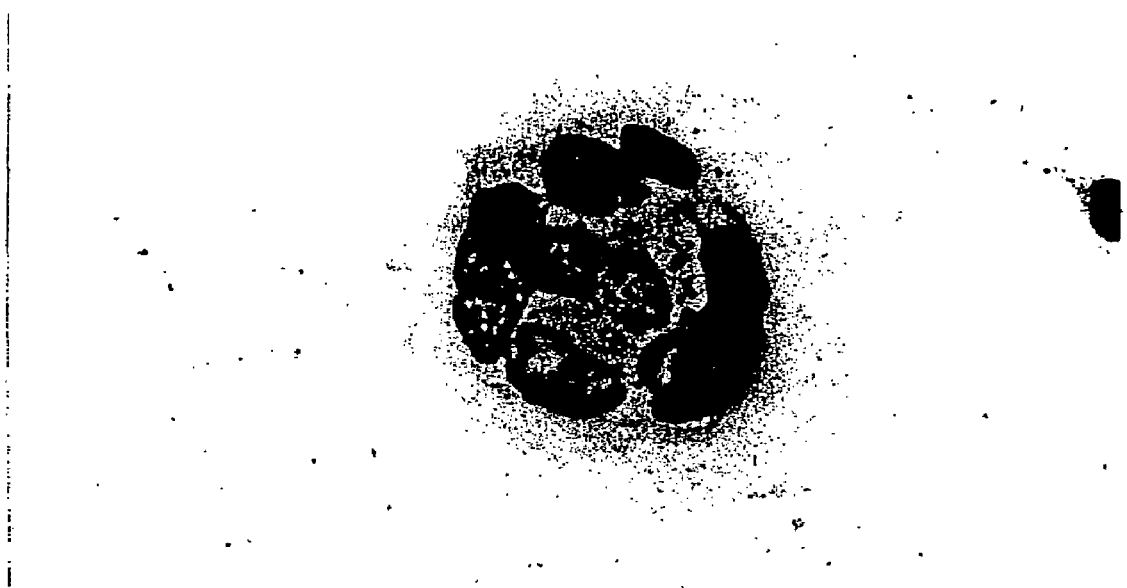
Figure 10D:
Figure 10E:
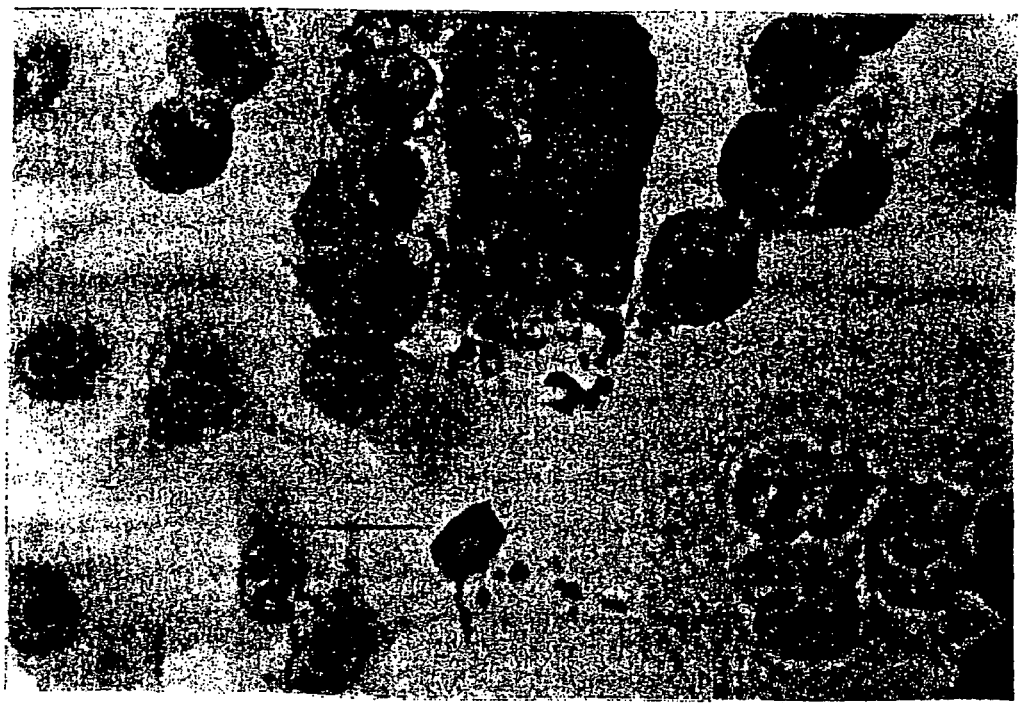
Figure 10F:

In another illustration of this embodiment the nucleotide sequence of the antisense RNA encoding HIV chemokine of SF-2 strain of HIV was deduced (SEQ ID NO:6) from the known nucleotide sequence of the minus strand. The first start codon is at nucleotide 52. The second start codon is at nucleotide 144. The larger protein (SEQ ID NO:7), starting at the first start codon has 112 amino acids and requires a (+1) frameshift at nucleotide 133 and −1 ribosomal frameshift at nucleotide 265. Another large protein (SEQ ID NO:14) is obtained by a (−1) frameshifting at nucleotide 133 and a (+1) frameshifting at nucleotide 265. If the sequence is read through, a protein of SEQ ID NO:15 is possible. Two shorter proteins are also possible starting at the second start codon. The first of these two (SEQ ID NO:8) has 82 amino acids and requires two (−1) ribosomal frameshifts at nucleotide 200 and nucleotide 265. The second of the shorter proteins (SEQ ID NO:9) has 81 amino acids and requires a ribosomal frameshift at nucleotide 201. It should be noted that both a 5' terminal hairpin, as well as pseudoknot motifs are present within the HIVaINR-generated antisense RNA (FIG. 9). These pseudoknots closely resemble synthetic RNA pseudoknots selected for binding to HIV-reverse transcriptase (Tuerk et al., 1992, Proc. Natl. Acad. Sci. USA, 89; 6988-6992). Similarly, sequences of antisense RNA of other strains of HIV can be deduced from the nucleotide sequence of the minus strand. These sequences are found to display at least 80% homology to the sequence of SEQ ID NO:6.

To further illustrate this embodiment, the nucleotide sequence of the antisense RNA encoding HIV chemokine of a HIV strain isolated from the CNS of a patient was deduced from the known nucleotide sequence of the minus strand (SEQ ID NO:25). The first start codon is at nucleotide 52. Depending upon the frameshifting or readthrough, multiple proteins are possible. For a (+1) frameshift at 133 nucleotide and (−1) frameshift at nucleotide at 265, a protein of SEQ ID NO: 10 is obtained. For a ribosomal frameshift of (−1) at nucleotide at 133, and a (+1) frameshift at nucleotide, a protein of SEQ ID NO:11 is obtained. If the frameshifts are read through, a protein of SEQ ID NO:15 is obtained.

In another illustration, the nucleotide sequence of the antisense RNA encoding HIV chemokine of a HIV strain isolated from the lymph node and spleen of a patient was deduced from the known nucleotide sequence of the minus strand (SEQ ID NO:26). The first start codon is at nucleotide 52. Depending upon the frameshifting or readthrough, multiple proteins are possible. For a (+1) frameshift at 133 nucleotide and (−1) frameshift at nucleotide at 280, a protein of SEQ ID NO: 12 is obtained. Additional amino acids are coded for in some variants. For a ribosomal frameshift of (−1) at nucleotide at 133, and a (+1) frameshift at nucleotide 280, a protein of SEQ ID NO:13 is obtained. If the frameshifts are read through, a protein of SEQ ID NO:16 is obtained.

Similarly, amino acid sequences for chemokine-like proteins from other strains of HIV can be obtained from the antisense RNA sequence. Thus, the amino acid sequence for (+1), (−1) frameshift for YU2 strain is disclosed in SEQ ID NO:16 and SEQ ID NO:17, while the amino acid sequence obtained by readthrough is SEQ ID NO:18.

The amino acid sequence of a chemokine-like protein for ELI strain with read through is disclosed in SEQ ID NO:19.

The amino acid sequence of a chemokine from another strain, p896, with several readthrough events is disclosed in SEQ ID NO:20.

It should also be noted that constructs which contain HIV LTR regions may also be used to produce HIV chemokines-like proteins. For example, the antisense RNA sequence of pHIV-CAT which is commonly used to transfect cells and was used to transfect cells as disclosed herein was obtained by standard sequencing techniques and is disclosed in SEQ ID NO:21. This antisense RNA encodes a protein SEQ ID NO:22.

Figure 2B:
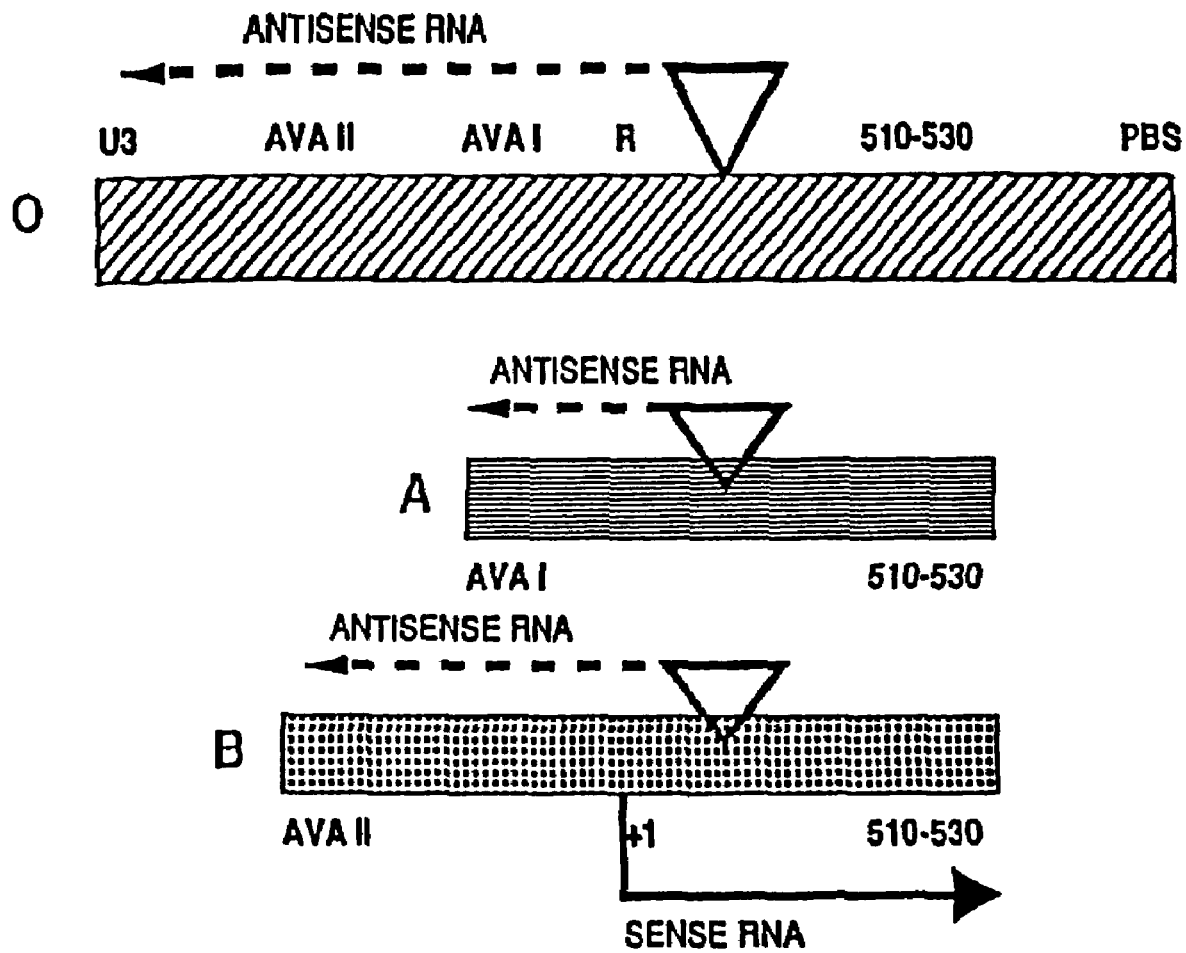
Figure 3A:
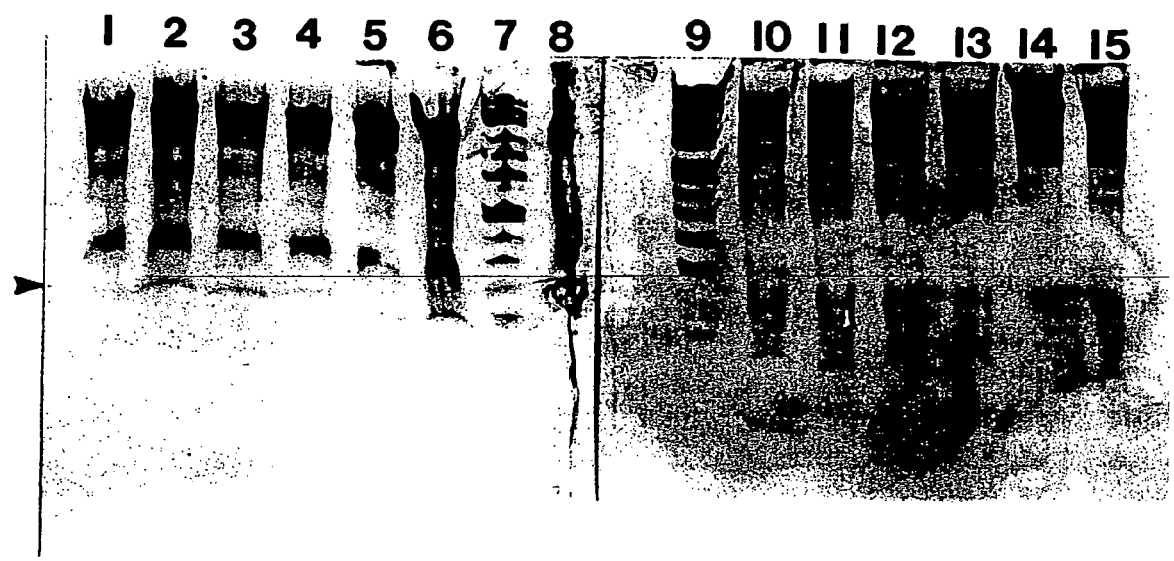
FIG. 3a and 3b are representations of the results of in vitro transcription reactions using a eukaryotic transcription system and the templates illustrated in FIGS. 2a and 2b.
Figure 3B:
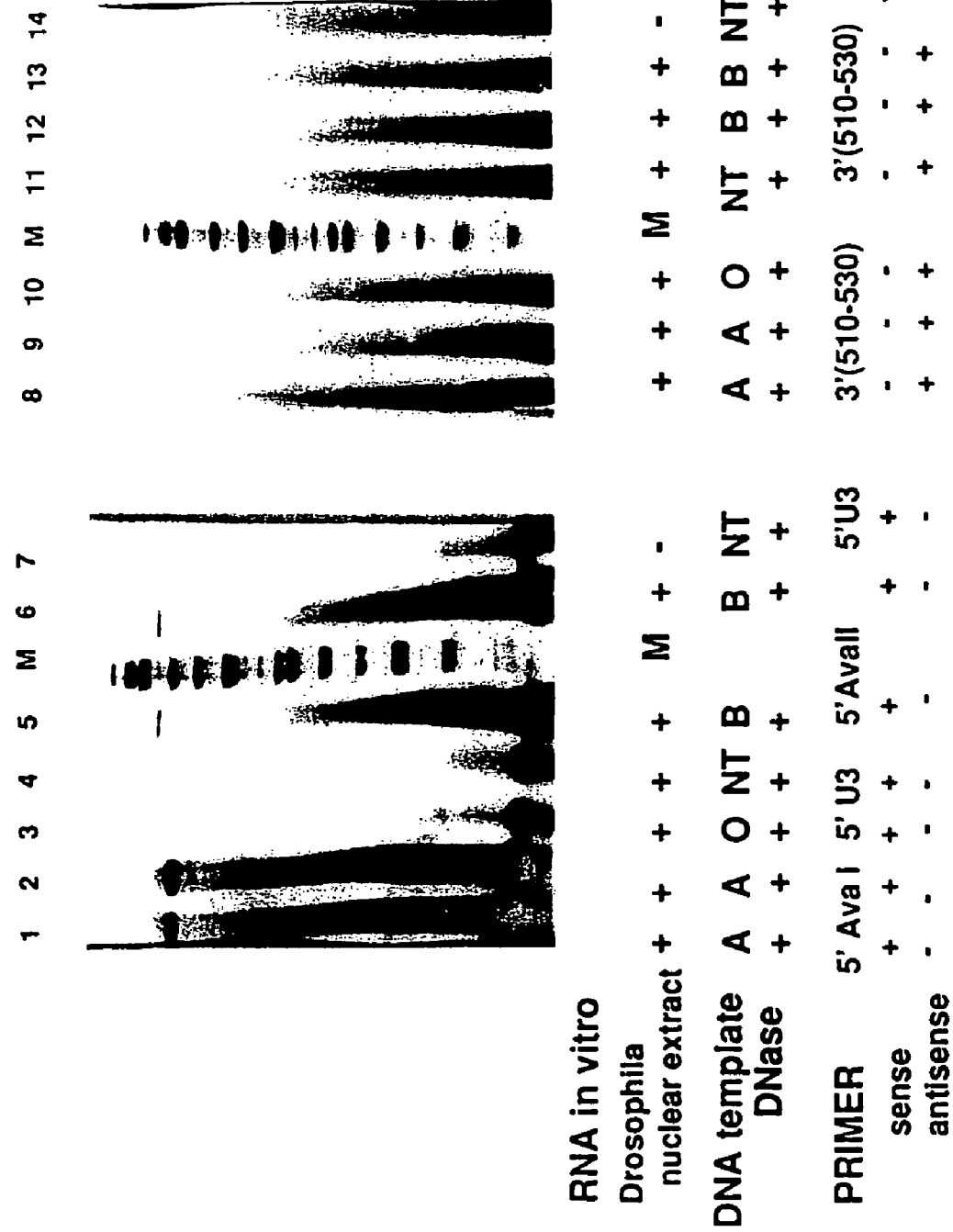

From these illustrations it will be evident to those skilled in the art that the sequence of the antisense RNA encoding chemokine-like proteins from HIV strains or double stranded constructs derived from the HIV strains, can be deduced. It will also be appreciated by those skilled in the art that the plasticity of the HIV genome leads to variations in the antisense RNA sequence. Such variations are intended to be included within the scope of this disclosure. Ribosomal frameshifting adds another element of plasticity to the sequence of encoded protein and is also intended to be within the scope of this disclosure.

In another illustration of this embodiment, the HIV chemokine gene including the open reading frame and HIV chemokine encoding sequence from different strains of HIV can be isolated. HIV dsDNA intermediate from an HIV-infected cell can be isolated or RNA transcripts may be amplified in vitro by reverse transcription from the HIV RNA by using oligonucleotide primers which specifically hybridize to the nucleotide sequence of SEQ ID NO:1. Using this sequence, it will be appreciated that one skilled in the art may design oligonucleotide primers useful in the nucleic amplification of the HIV chemokine gene, or oligonucleotide probes useful for detection of amplified sequences containing all or a portion of the HIV chemokine-like protein encoding sequence in other strains of HIV isolated from different individuals or of HIV isolated from different tissues of the same individual.

A further alternative is to isolate either HIV RNA or HIV dsDNA from HIV-infected cells using methods known to those skilled in the art, and then use techniques that would result in the amplification and/or cloning of an HIV chemokine coding sequence. Following determination of the nucleotide sequence of the isolated HIV chemokine, further characterization may be performed by computer analysis using software known in the art to record the DNA sequence and determine the correct reading frame, codon usage, predicted amino acid sequence and molecular size of the encoded HIV chemokine, and comparison of the amino acid sequence of that particular HIV chemokine with the amino acid sequence of other HIV chemokines.

Example 2

This embodiment illustrates the generation of HIV chemokine RNA transcripts off of the antisense initiator, HIVaINR. Since HIV-1, once integrated into a human host cell chromosomal DNA, is dependent upon eukaryotic transcription-factors and RNA polymerases to transcribe its genes (Cullen, 1992, Microbiol. Reviews, 375-394), a eukaryotic transcription system (commercial *Drosophila* embryo nuclear extract transcription system) that can efficiently transcribe from eukaryotic initiators in vitro was used to investigate whether eukaryotic transcription could initiate from the HIVaINR. Four different HIV-1 LTR fragments, illustrated in FIG. 2*a*, were generated by polymerase chain reaction using HIV-LTR templates and primers containing bacteriophage T7 or Sp6 polymerases, as previously described (Ludwig et al., 1995, Nuc. Acid Res. 23:3792-3793), which method is hereby incorporated by reference. The fragments are 5'Hae III PBS (Sp6) 3' which includes two Sp1 sites and TATA box and extends through the primer binding site (PBS; Fragment 1); 5' PvuII-PBS (Sp6) 3' fragment which lacks all of the Sp1 sites and bisects the TATA box (Fragment 2); 5' (T7) PvuII-SacI (Sp6) 3' fragment which truncates the TAR region 48 base pairs from the mRNA cap site and start site (Fragment 3); and 5' (T7) R-BssHII (Sp6) 3' fragment which contains no HIV-1 promoter Sp1 sites or TATA box but contains the TAR region DNA (Fragment 4).

In vitro transcription reactions were performed with each template using a eukaryotic transcription system (*Drosophila* Nuclear Extract, Promega) according to manufacturer's instructions, to initiate transcription off of HIVaINR. This eukaryotic transcription system used *Drosophila* nuclear extracts to supply transcription factors and the eukaryotic RNA polymerases. Each of the in vitro transcription reactions was then treated with DNase I to remove DNA template, followed by phenol chloroform extraction and by ethanol precipitation to remove the DNase from the synthesized RNA. The RNA transcripts were hybridized either to a biotin-labeled sense RNA probe (5' (T7) R-U5-PBS-BssH II (SP6) 3') FIG. 3*a*, lane 1-6 or to biotinylated antisense RNA probe (5' (SP6) BssH II-PBS-U5-R (T7) 3') FIG. 3*a*, lanes 10-15. The hybridized RNA was subjected to ribonuclease T1 digestion and analysis by electrophoresis on a denaturing 8% polyacrylamide gel electrophoresis (PAGE). The size of RNA transcript was observed to be 25 nucleotides distinct from the protected TAR loop or undigested probe (FIG. 3*a*, lanes 2-6; which was absent in control lane 1).

As shown in lanes 10-15, FIG. 3*a*, no expected size transcripts were initiated in the usual sense orientation, as demonstrated by the failure of the antisense probe to hybridize, and thereby protect, sense transcripts in a RNA digestion assay. It is important to note that for the in vitro transcription experiments, *Drosophila* nuclear extracts were used, which intrinsically lack Sp1 protein. Thus a major driving force for sense transcription from the HIV-1 promoter in vitro was lacking, enabling the observance of antisense transcription in isolation. It was observed that primer extension utilizing HIV-specific biotinylated primers and unlabeled dNTPs allowed specific analysis of the RNAs synthesized off the HIV LTR templates while eliminating the background contribution seen from the *Drosophila* nuclear extract (FIG. 3b). Simultaneous in vitro transcription reactions performed using *Drosophila* nuclear extract and either the original HIV-1 LTR (labeled O), or truncated portions of the HIV-1 LTR extending from the AvaI to the HindIII site. (labeled A), or extending from the AvaII to the HindIII site (labeled B), as diagrammed in FIG. 2b) allowed delineation of the 3' end of the antisense transcript between the AvaII site and the U3 end of the HIV-1 LTR (FIG. 3b). Control transcription reactions receiving no template were labeled NT. Primer extension with sense AvaI or Ava II primers, with RNA synthesized from the truncated A or B templates demonstrated cDNA of the expected size for an antisense transcript generated off the HIV aINR.

Example 3

This embodiment is directed towards demonstration of in vivo transcription from HIV-aINR. An in vivo eukaryotic transcription system may be used to produce mRNA transcripts from human cell lines (e.g., a lymphoid cell line such as Jurkat T cells, or a mononuclear phagocyte cell line) which have been transfected with a eukaryotic vector containing the coding sequence for HIV chemokine operably linked to the HIV antisense initiator or other functional eukaryotic promoter including one or more regulatory elements.

To further illustrate this embodiment, in vivo transcription from the HIV-aINR was analyzed by reverse transcription-polymerase chain reaction of RNA isolated from human Jurkat T cells which has-been transfected with pHIV-CAT. Plasmid pHIV-CAT contains the HIV-1 LTR U3 and R sequences 5' to the chloramphenicol acetyltransferase (CAT) gene. Transfections of plasmid DNA were performed in the presence of a transfection agent (Transfectam™, Promega). Briefly, plasmid DNA (0.086 µg plasmid DNA per 0.182 µl transfectum per well for 2 hours) was incubated with the cells using conditions as essentially described by the manufacturer. Control transfection reactions included pHIV-CAT plus pSV-βgal plus transfection reagent (to assess transfection efficiency), transfection reagent alone ("mock" transfection), or no treatment at all. Cells were then resuspended in culture medium and continued in culture for two days. RNA was then extracted from the pelleted cells, and purified using standard techniques well known in the art. The purified RNA was then split and subjected to reverse transcription using a 5' AvaI sense primer (SEQ ID NO: 3), to anneal with and extend HIV-antisense transcripts, followed by amplification by PCR with 30 cycles of denaturing (94°, 45 seconds), reannealing (70° C., 45 seconds), and extension (72° C., 2 minutes) using the Ava1 sense primer and either a 3' antisense primer (SEQ ID NO:4), or a 3' Mae1 antisense primer (SEQ ID NO:53). The reverse-transcription-PCR products were then analyzed by 3% agarose gel electrophoresis, transferred to a nitrocellulose membrane (Biodyne) and detected colorimetrically.

Figure 4:
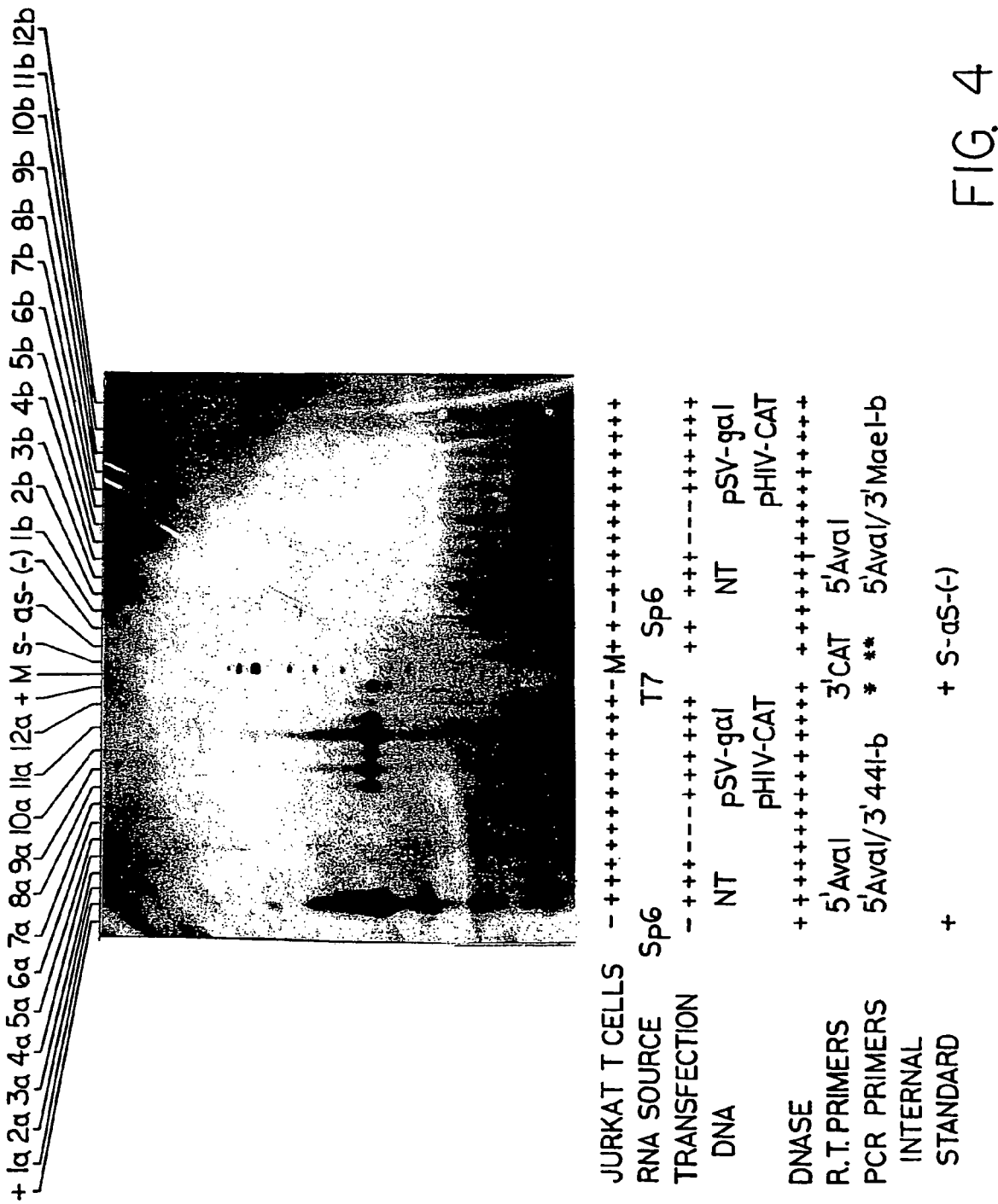
FIG. 4 is a representation of the results of in vivo transcription reactions followed by analysis of RNA using reverse transcription and polymerase chain reaction in Jurkat T cells transfected with the HIV LTR CAt vector or control transfections.
Figure 6:
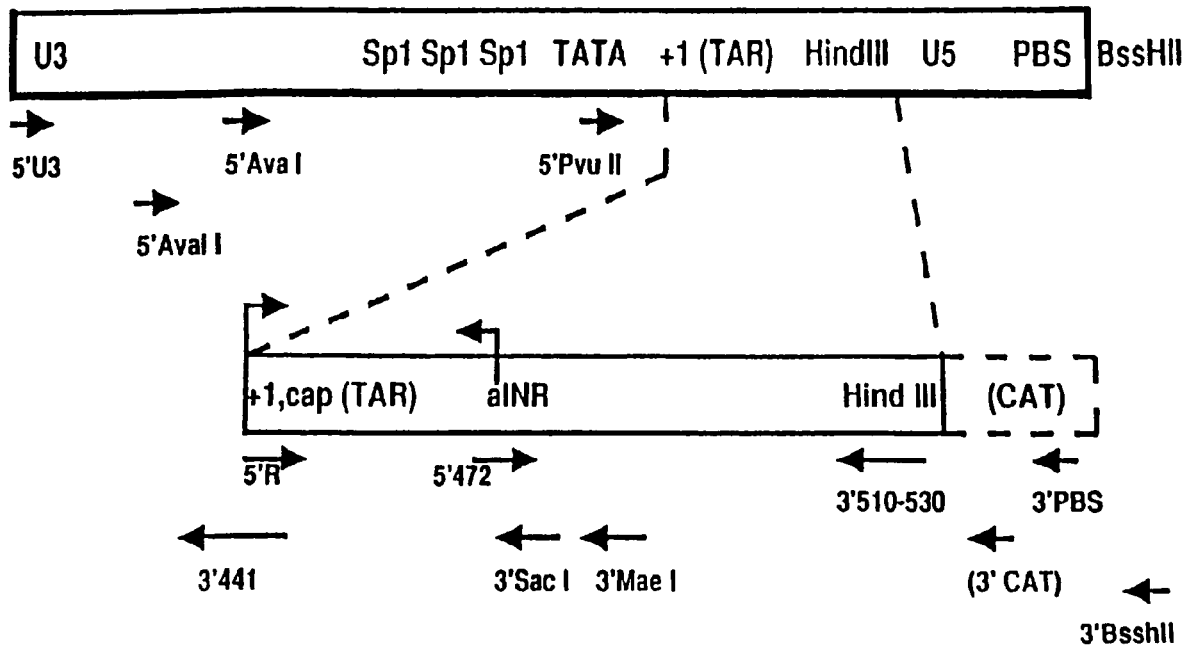
FIG. 6 is a schematic representation of the HIV-1 LTR showing various regulatory elements and bidirectional transcription initiation sites, as well as primers utilized in RNA analysis by RT-PCR.

The results are illustrated in FIG. 4. The lanes marked "M" represent DNA size standard markers. HIV-1 RNA transcripts could be detected only in RNA isolated from Jurkat T cells transfected with pHIV-CAT (FIGS. 4, 7a-12a), using a 5' sense primer (5' AvaI) to extend off the antisense transcript in the reverse transcription reaction, followed by PCR amplification with the 5'AvaI sense primer and a biotinylated antisense 3' 441 primer containing sequences complementary to beginning TAR sequences. As shown in FIG. 4, lanes 1a-3a), no product was obtained in simultaneous identical reverse-transcription PCR reactions performed using total cellular RNA isolated from Jurkat T cells that were mock transfected, and received transfectam but no DNA template (NT). No products were obtained when the same samples as in lanes 7a-12a in FIG. 4, were simultaneously analyzed by reverse transcription PCR with 5' AvaI in the reverse transcription step, but amplified with an alternative 3' MaeI antisense primer during PCR (lanes 7b-12b). The 3' MaeI antisense primer is complementary to sequences in TAR region situated beyond the HIV aINR (FIG. 6), and is therefore, not expected to generate amplified products from authentic antisense RNA. This control, therefore, serves to confirm the authenticity of transcripts originating from the HIVaINR.

In another illustration of this embodiment cells stably transfected with HIV were used to demonstrate the presence of transcripts originating from the HIVaINR. Therefore, cell line U38 containing stably transfected HIV-1 LTR-CAT gene sequences were analyzed for in vivo antisense HIV-1 transcripts. The cells were cultured with or without stimulation with calcium ionophore and phorbol ester. Total RNA was extracted by standard methods, split equally three ways and treated either with a single DNase treatment, two DNase treatments, or two DNase treatments plus RNase digestion. The samples were then subjected to reverse transcription-PCR. For reverse transcription PCR analysis, each treated sample was analyzed five ways: for the presence of antisense HIV-1 transcripts (FIGS. 5a and 5b, lanes 2-7); for the presence of sense HIV-1 transcripts (FIGS. 5a and 5b, lanes 28-33); for the presence of DNA contamination (FIGS. 5a and 5b, lanes 20-25); for G3PDH RNA (FIG. 5b, lanes 37-42); and for reverse transcription PCR performed without the reverse transcriptase (FIGS. 5a and 5b, lanes 11-16. Internal controls, consisting of primer without template (FIG. 5, "Pr", lanes 8, 17, 26, 34 and 43) were also run to confirm that the reverse transcription-PCR reaction mixture were not contaminated with templates. A separate control set with primers and an internal control standard RNA template (FIG. 5, "Is", lanes 1, 10, 19, 27, and 36) was run to confirm comparable primer annealing efficiency. In addition, RT+/− and PCR (kit)+/−kit controls were run in lanes 44-47. Thus, FIG. 5a illustrates the biotin-labeled RT-PCR products following transfer to a membrane and colorimetric detection (G3PDH primers were not labeled), and 5b illustrates the RT-PCT products as photographed following ethidium bromide staining of the gel prior to transfer.

Figure 5A:
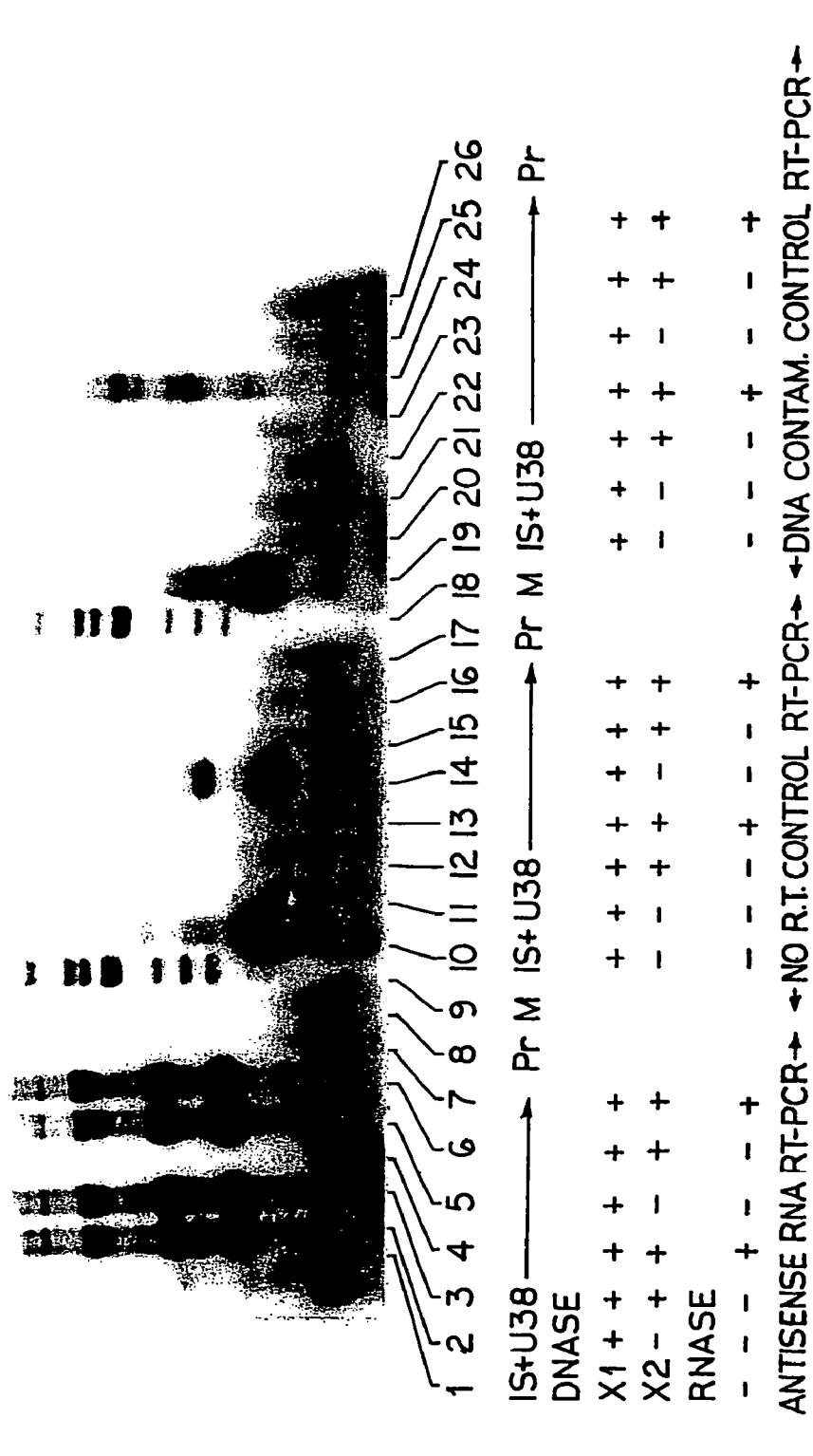
FIGS. 5a and 5b are representations of the isolation of RNA transcripts originating off of the antisense initiator in stably transfected cells.
Figure 5A:
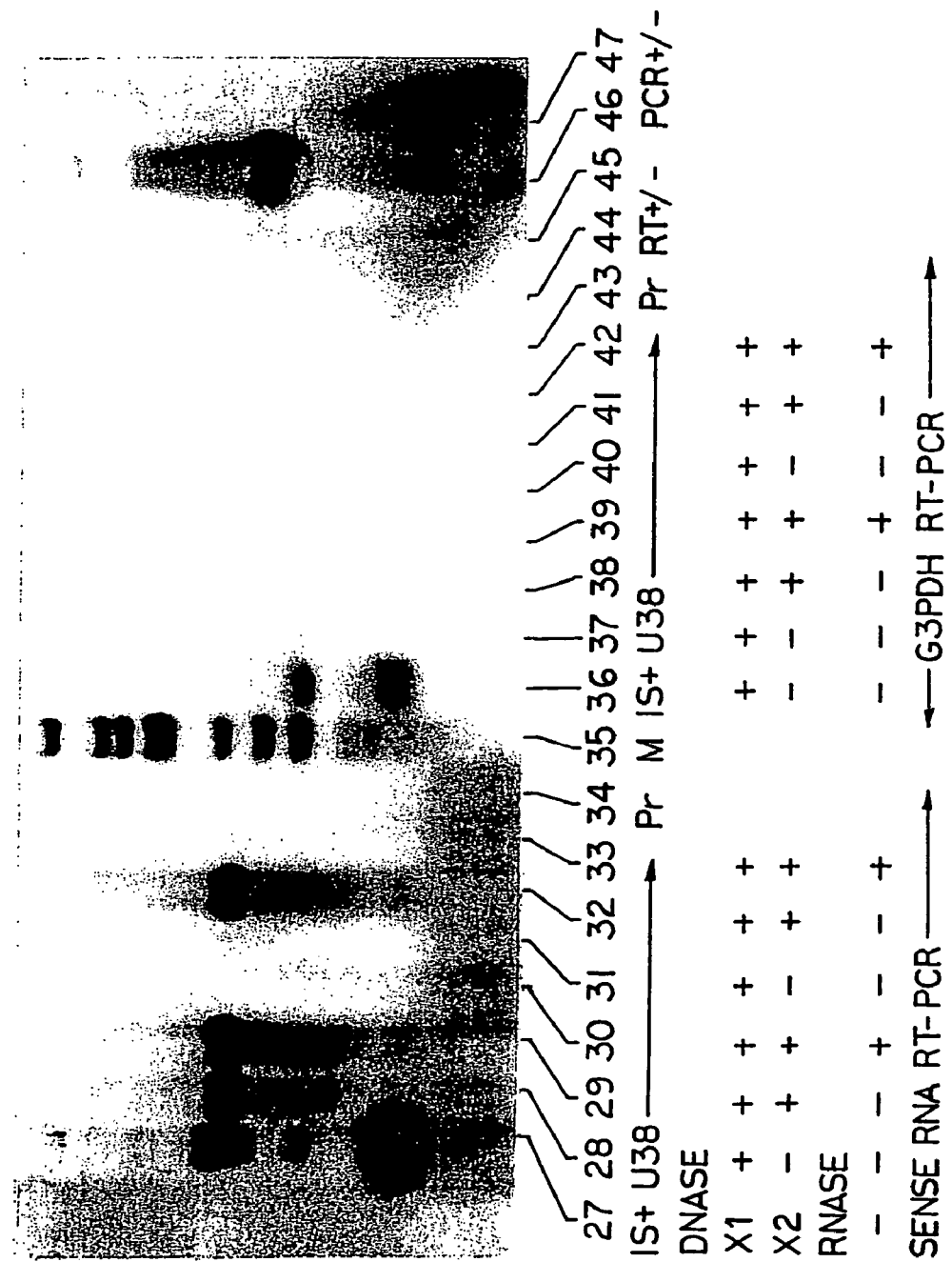
Figure 5B:
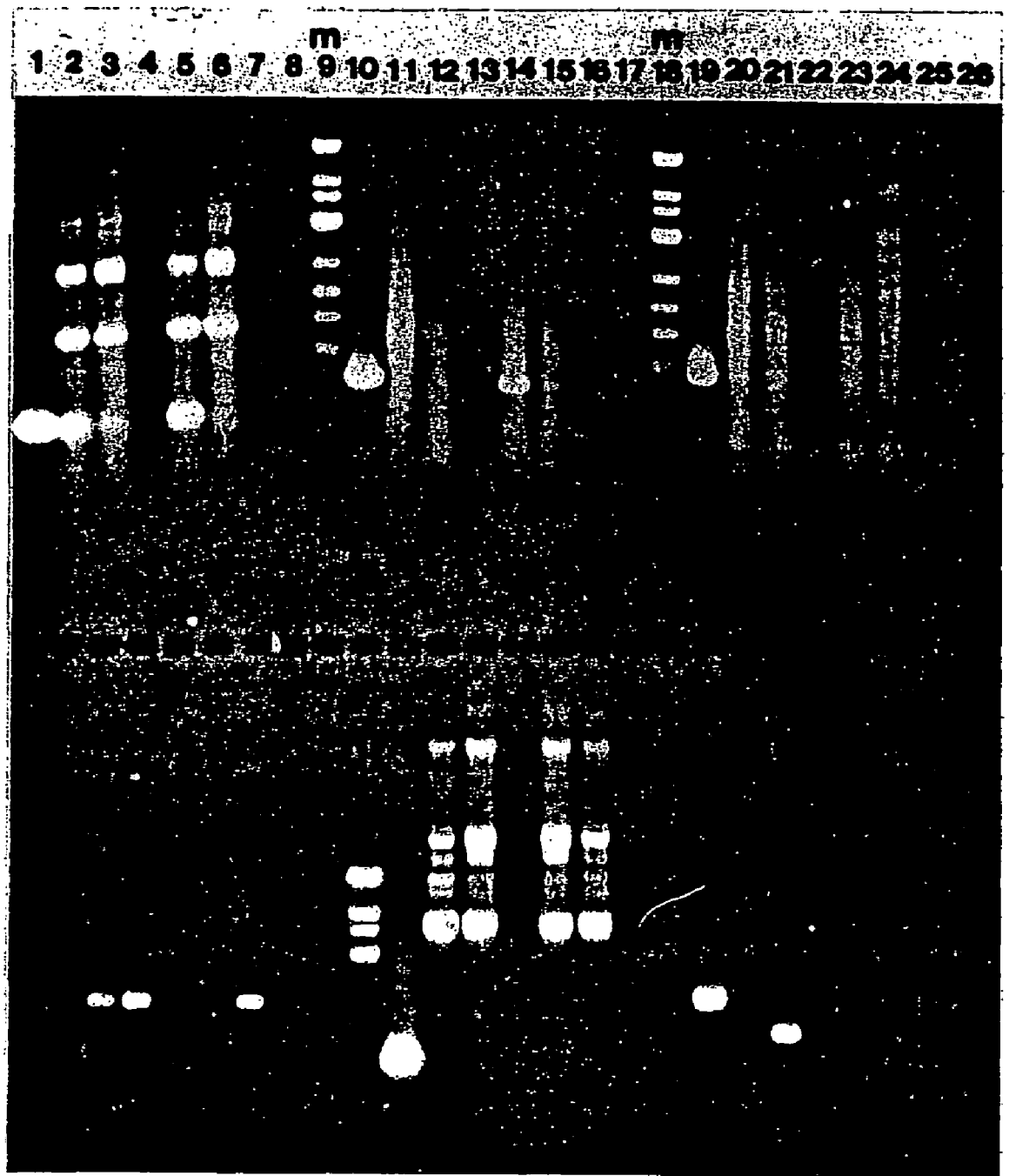

As shown in FIGS. 5a and 5b, antisense RNA transcripts are made off of the HIVaINR in stably transfected cells in vivo, at a level (lanes 2-7) comparable to intrinsic cellular G3PDH RNA transcripts (FIG. 5b, lanes 37-42) and sense HIV-1 transcripts (lanes 28-33). RNase digestion (lanes 4 and 7), but not DNase digestion (lanes 2, 3, 5 and 6) of the U38 total cellular RNA eliminated the antisense RNA product band(s) of reverse transcription-PCR reactions. The identical RNA samples that had RNase treatment also demonstrated the elimination of products for G3PDH RNA (FIG. 5b, lanes 39 and 42, and for sense HIV RNA lanes 30 and 33). Antisense RNA generated off the HIV-1 LTR and analyzed by reverse transcription using sense primer (5' AvaI) generated a cDNA when the sense 5' primer or the antisense 3' 441 primers were present in the PCR reaction but not when an antisense MaeI primer was present in the PCR reaction. The MaeI primer anneals outside of the transcription start site for antisense RNA. Third, while DNA contamination can be observed with U38 total cellular RNA samples obtained from cells stimulated with Ca ionophore and PMA, and treated with DNase only once (FIGS. 5a and 5b, lane 14), no contamination was observed with any of the total cellular RNA samples obtained from unstimulated U38 (FIGS. 5a and 5b, lanes 11-13, which correspond to the same RNA samples analyzed in lanes 2,-4).

In summary, this embodiment demonstrates the generation of authentic antisense transcripts in vitro and in vivo.

Example 4

An HIV chemokine according to the present invention may be characterized by its amino acid sequence, which may vary depending on the HIV isolate of origin, including tissue site of the HIV isolate of origin. By using nucleotide sequence data, the amino acid sequence of the HIV chemokine protein, as shown in SEQ ID NO:2 for lbl revINRold, SEQ ID: NOs: 7, 8 and 9 for SF-2 strain is derived.

In one illustration of this embodiment, using a gene database, and a software alignment program known in the art, a sequence comparison was made between a HIV chemokine amino acid sequence and various mammalian chemokines. FIG. 7 illustrates a comparison of the deduced amino acid sequence of HIV chemokine of the present invention and other chemokines. After introducing gaps in the SDF-1 sequence, a consensus was obtained for 23 of the amino acids of HIV chemokine (lbl revINRold; SEQ ID NO:2) and SDF-1; for 20 of the amino acids of HIV chemokine (lbl revINRold; SEQ ID NO:2) and IL8-human, and HIV chemokine and I-309 (FIG. 7). The α-chemokine receptor CXCR4 has been identified as a coreceptor required for HIV entry, and one natural ligand for CXCR4 has been identified as CXC chemokine SDF-1. Thus, the relatedness of the HIV chemokine to SDF-1, as shown in FIG. 7, implicates the HIV chemokine as being α-factor (alone) or a cofactor (with gp120) in binding to chemokine receptors required for HIV entry into a target cell. That SDF-1 has been shown to inhibit infection of CXCR4 and CD4 expressing cells by T-tropic HIV-1 strains (Oberlin et al., 1996, supra) suggests that isolated and purified HIV chemokine may also inhibit infection of CXCR4 and CD4 expressing cells by HIV-1 strains. Based on these findings, the HIV chemokine may be used to generate peptides or a modified variant of the HIV chemokine for use as a vaccine; as an antigen to generate antisera such as for neutralizing antibodies and for diagnostic immunoassays; as an agonist of HIV chemokine; as an antagonist to HIV chemokine and to generate primers or probes from the corresponding HIV chemokine coding sequence for diagnostic and prognostic applications.

In another illustration of this embodiment, the amino acid sequences of HIV chemokines from different strains of HIVs was deduced from their known nucleotide sequences of the minus strand available from gene databases. Using commercially available software, the amino acid sequence of HIV chemokines transcribable from the plus strand was compared for cell lines and HIV isolates from patients. The cell lines compared were TCLA, SF-2, macrophage trophic primary viral (YU2). The data from HIV isolates of patients was obtained from either central nervous system ((Pt)CNS) or lymph node and spleen isolates ((Pt)LN/SP. As illustrated in FIG. 8, the amino acid sequence of the HIV chemokines shows a high degree of homology with the N-terminus being more conserved. Although the amino acids comprising this portion of the amino terminus of all HIV chemokines analyzed to date seem to be conserved, one skilled in the art will appreciate that minor variations in the amino acid sequence may occur, particularly since HIV is known to frequently vary its sequences. However, the comparison suggest that the conservation of this region may reflect a common mechanism for structure (e.g., folding) or for regulation. The plasticity of the RNA (secondary tertiary structures i.e. pseudoknots) enables more than one potential reading frame to be utilized.

Example 5

The present invention relates to an HIV gene, isolated from a strain of HIV, wherein the gene encodes an HIV chemokine-like protein. With sequence information, like that shown in SEQ ID NOs: 1 and 2, other polypeptides can be produced which display "HIV chemokine" activity. More particularly, variant nucleotide sequences can be natural variants or variants produced by synthetic or mutagenic means for modifying the disclosed nucleotide sequences. Methods for synthetically producing such variant sequences are known to those skilled in the art of protein design. In designing such variants, one needs to consider avoiding mutations of sequences that encode the structurally and functionally-involved amino acids, or the cysteine residues involved in disulfide bond formation, which may negatively affect the role of the HIV chemokine in binding to chemokine receptors. In that regard, it is noted that the receptor-binding pocket (also called the "hydrophobic pocket") is a domain of the HIV chemokine involved in binding to chemokine receptors. The domain can be determined using methods known in the art in which chimeras of chemokines, in which domains are interchanged, are tested for their ability to bind to a specific receptor (Heinrich and Bravo, 1995, J. Biol. Chem. 270:28014-7; Hammond et al., 1996, J. Biol. Chem. 271:8228-35). These standard techniques have been used to determine which binding domain(s) can function as an agonist, partial agonist, or an antagonist (Heinrich and Bravo, 1995, supra). Thus, the potential domains of HIV chemokine, resembling that of other chemokines can be interchanged with similar domains of SDF-1 in forming chimeras whose binding specificity to CXCR4 (or CXCR4 and CD4) expressing cells can then be evaluated using methods known in the art (Oberlin et al., 1996, supra, Bleul et al., 1996, supra). Similarly, chimeras made of domains of HIV chemokine with another chemokine (e.g., RANTES or MIP-1α, or MIP-1β) and tested against β-chemokine receptor expressing cells (CCR-5, or CCR2b, or CCR3) may be used to determine the domain(s) of HIV chemokine that can function as an agonist, partial agonist, or an antagonist. Analysis of chimera binding to β-chemokine receptor expressing cells has been described previously (see, e.g., Rucker et al., 1996, Cell 87:437-446). Identifying the amino acids making up a HIV chemokine functional domain in binding specificity to a chemokine receptor enables the design of peptides or modified variant HIV chemokine which may be useful for therapeutic and/or diagnostic applications.

In one embodiment, the variant sequence may be produced by site-directed mutagenesis using one of the several methods for such mutagenesis which are known to those skilled in the art (see, e.g. U.S. Pat. No. 5,397,705). For example, site directed mutagenesis using oligonucleotides comprises the steps of (i) synthesizing an oligonucleotide with a sequence nearly identical to a sequence in the HIV chemokine gene except that the oligonucleotide sequence contains the desired nucleotide substitution (encoding for a mutation in the amino acid sequence); (ii) hybridizing the oligonucleotide primer to a template comprising the nucleotide sequence encoding an HIV chemokine; and extending the oligonucleotide primer using a DNA polymerase. The resultant variant sequence may then be incorporated into an expression vector which is then used to genetically engineer a host cell to recombinantly produce a polypeptide having at least partial, if not full, HIV chemokine binding specificity.

In another embodiment, genetic engineering techniques can be used to generate nucleic acid molecules comprising a variant sequence that is a substantial portion of the HIV chemokine gene. As apparent to one skilled in the art, from the HIV chemokine gene sequence, and from a restriction map thereof, it can be determined which restriction enzyme or combination of restriction enzymes may be used to generate nucleic acid molecules encoding a modified variant of HIV chemokine having some of, the same as, or more than, the binding specificity exhibited by the HIV chemokine of natural HIV isolates. Restriction enzyme selection may be done so as not to destroy the binding domain/hydrophobic pocket of the resultant polypeptide. Consequently, restriction enzyme combinations may be used to generate nucleic acid molecules (variant sequences), which when inserted into the appropriate vector, are capable of directing the production of a modified variant of HIV chemokine having some of, the same as, or more than, the binding specificity exhibited by the HIV chemokine of natural HIV isolates.

In a further embodiment, an HIV chemokine may be made into a modified variant of HIV chemokine by chemical means. For example, a modified variant (a "derivative") of the chemokine RANTES was created by chemical modification of the amino terminus (Simmons et al., 1997, Science 276: 276-279). The amino terminus was modified by reacting it with aminooxypentane (AOP). The resultant AOP-RANTES was a potent antagonist which inhibited infection of target cells by M-tropic HIV-1 strains (indicating full receptor occupancy), yet did not induce chemotaxis. Thus, the amino terminus of HIV chemokine may be reacted with AOP by amino terminal oxidation using the methods described by Simmons et al. (supra) to achieve a modified variant of HIV chemokine that may act as an antagonist.

Example 6

This embodiment illustrates that a nucleic acid molecule comprising a nucleotide sequence encoding an HIV chemokine, a variant sequence encoding a modified variant HIV chemokine, or a nucleotide sequence encoding a peptide derived from HIV chemokine (collectively referred to as "nucleotide sequence), can be inserted into a vector for expression in a host cell system. Successful expression of the HIV chemokine, modified variant HIV chemokine, or peptide derived from HIV chemokine (collectively referred to as "recombinant HIV chemokine"), requires that either the insert comprising the nucleotide sequence encoding the recombinant HIV chemokine, or the vector itself, contain the necessary elements for transcription and translation (regulatory elements) which is compatible with, and recognized by the particular host system used for expression. A variety of host systems may be utilized to express the recombinant HIV chemokine, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, the antisense initiator, aINR, or other promoters and regulatory elements can be incorporated into the vector or the nucleotide sequence encoding the recombinant HIV chemokine, to increase the expression of the recombinant HIV chemokine, provided that this increased expression is compatible with (for example, non-toxic to) the particular host cell system used. The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the nucleotide sequence and expression into the recombinant HIV chemokine product. For example, bacterial, phage, or plasmid promoters known in the art from which a high level of transcription has been observed in a host cell system comprising E. coli include the lac promoter, trp promoter, tac promoter, recA promoter, ribosomal RNA promoter, the $P_R$ and $P_L$ promoters, lacUV5, ompF, bla, lpp, and the like, may be used to provide transcription of the inserted nucleotide sequence encoding the recombinant HIV chemokine. Promoters known in the art for transcription to occur in mammalian cells may include viral or viral-like basal promoters like the SV40 late promoter, the RSV promoter, the CMV immediate early promoter, adenovirus major late promoter, the MMTV promoter, and a VL30 promoter; and cellular promoters including metallothione promoters (See, e.g., Larsen et al., 1995, Nucleic Acids Res. 23:1223-1230; Donis et al., 1993, BioTechniques 15:786-787; Donda et al., 1993, Mol. Cell. Endocrinol. 90:R23-26; and Huper et al., 1992, In Vitro Cell Dev. Biol. 28A:730-734), and may be used to provide transcription of the inserted nucleotide sequence encoding the recombinant HIV chemokine.

Other regulatory elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted nucleotide sequence encoding the recombinant HIV chemokine to increase transcriptional efficiency. One or more regulatory elements, such as transcription or translation initiation signals, may be used to regulate the expression of the nucleotide sequence encoding the recombinant HIV chemokine. Such regulatory elements may be inserted into the nucleotide sequence encoding the recombinant HIV chemokine or nearby vector DNA sequences using recombinant DNA methods described for insertion of DNA sequences.

Accordingly, a nucleotide sequence encoding for a recombinant HIV chemokine can be ligated into an expression vector at a specific site in relation to the vector's promoter and regulatory elements so that when the recombinant vector is introduced into the host cell, the recombinant HIV chemokine is expressed from the recombinant vector in the host cell. For example, the nucleotide sequence containing its own regulatory elements can be ligated into an expression vector in a relation or orientation to the vector promoter, and control elements which will allow for expression of the recombinant HIV chemokine. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker or auxotrophic marker) present in the vector; immunoscreening for production of recombinant HIV chemokine-specific epitopes using antisera generated to epitopes of HIV chemokine; probing the DNA of the host cells for a nucleotide sequence encoding a recombinant HIV chemokine using one or more oligonucleotides, and methods known in the art; and a functional assay to test binding of the recombinant HIV chemokine to a chemokine receptor which is known to bind to HIV chemokine.

Example 7

This embodiment demonstrates the effects of introducing the gene sequence for the HIV chemokine(s) into a cell line. To illustrate this embodiment, a cell line stably producing multiple HIV-1 proteins but no infectious virus was used (HL2/3; Ciminale et al., 1990, AIDS Research and Human Retroviruses, vol 6, p 1281-1286). HL2/3 was generated by stably transfecting HeLa cells with a hybrid HIV-1 clone HXB2/3gpt and selecting for stable production of HIV-1 proteins. Gag, Env, Tat, Rev, and Nef, but no reverse transcriptase, are produced by this cell line and co-cultivation experiments demonstrate no viral propagation. It was intended as a fusion partner, along with another cell line expressing CD4 (HLCD4-CAT). No CD4 is expressed on the surface of the HL2/3 cell line as determined by flow cytometry.

HeLa cells (3.8×105/well) were plated and then transfected the following day for 2 hours, followed by the addition of serum containing media and various treatments. A comparison of cells following either mock transfections (Transfectam, Promega) or transfections with either pHIV-CAT (abbreviated pHIV; Nable et al., 1987, Nature, 326:711-713), or pwtΔ (Rizzuto et al., 1998, Science, 280:1949-53 and pHIV-CAT (abbreviated as pHIV+pwt) performed as described in Example 3, illustrates the effects of the HIV-1 LTR U3 and R sequences (containing the HIV chemokine gene) on cell survival and morphology (Table 1 and FIG. 10). Sequencing of the constructs indicated that plasmid pHIV-CAT contains the HIV-1 LTR U3 and R sequences 5' to the CAT gene, whereas the plasmid pwtΔ contains a truncated gp-120 construct (Sodroski et al.) as well as the HIV-1 LTR. HL2/3 cells, following transfection, were +/−stimulated with Ca ionophore (50 ng/ml) and phorbol myristate acetate (50 ng/ml) or treated or not with affinity-purified rabbit antibody to HIV chemokine peptides (+Ab) and grown on coverslips for hematoxylin and eosin staining in 6-well plates. Four peptides were used together for generating the antibodies. These were peptide corresponding to amino acid 19-35 of SEQ ID NO:10, amino acid 51-71 of SEQ ID NO:2, amino acid 89-103 of SEQ ID NO:10 with a cysteine at N-terminal end, and amino acid 20-38 of SEQ ID NO:2. After 3 days, the coverslips were removed for staining and cell counts and viability were assessed by trypan blue exclusion. Cell morphology was assessed by phase contrast microscopy in the well and following staining (FIG. 10).

TABLE 1

| GROUP | TREATMENT | TOTAL CELLS × $10^5$/ ALIVE × $10^5$ | % DEAD | COMMENTS |
|---|---|---|---|---|
| 1 | Mock, unstim. | 4.6/4.5 | 1 | normal HeLa |
| 2 | Mock, unstim; Ab | 9.7/9.5 | 1 | normal HeLa; increased |
| 3 | Mock, stim + Ab | 7.1/6.9 | 1 | normal cellular +/− clumps |
| 4 | pHIV, stim + Ab | 5.1/2.8 | 45 | pyknotic cells, giant cells |
| 5 | pHIV + pwt, stim + Ab | 3.6/1 | 72 | ++clumps, pyknotic, syncytium |

TABLE 1-continued

| GROUP | TREATMENT | TOTAL CELLS × $10^5$/ ALIVE × $10^5$ | % DEAD | COMMENTS |
|---|---|---|---|---|
| 6 | Mock, stim | 2.1/2.0 | 2 | less cellular, few mitosis |
| 7 | pHIV, stim | 1.3/1.1 | 15 | less cellular, +/−pyknotic |
| 8 | pHIV + pwt, stim | 1.2/0.9 | 25 | +clumps, pyknotic |

When representative coverslips from the above groups were stained and examined the following observations were made. Mock stimulated cells (Group 6; FIG. 10A) were present in a monolayer with relatively uniform round to oval nuclei, low nuclear to cytoplasm ratio, abundant stellate amphophilic cytoplasm with cytoplasmic processes. Cellular nuclei contained finely granular, evenly distributed chromatin (1-3 prominent nucleoli). Scattered binucleated cells were also observed. For pHIVCAT transfected and stimulated cells (Group 7; FIG. 10B); viable cells with nuclear and cytoplasmic features similar to those in control (FIG. 10A) were observed. However, there were numerous degenerated cells that contained pyknotic, shrunken nuclei and eosinophilic cytoplasm (apoptotic). For pHIVCAT+pwtΔ transfected and stimulated cells (Group 8; FIG. 10C), only a few cells were present. A single syncytium is shown in FIG. 10C consisting of pyknotic nuclei and eosinophilic cytoplasm. Some nuclei with partially clumped chromatin can also be seen.

For mock transfected, stimulated cells that received antibody to peptides 1-4 (Group 3; FIG. 10D), cells were in a monolayer and similar to Group 6. However, the cytoplasm appeared more vacuolated, and nucleoli were prominent and angulated. FIG. 10D shows a single quadripolar mitotic figure. For cells transfected with pHIVCAT+pwtΔ, stimulated, and receiving antibody (Group 5; FIG. 10E), syncytium was present but the nuclei were all shrunken and pyknotic. The nuclear to cytoplasmic border was not discernable. Some of the uninucleate cells appeared to have somewhat shrunken nuclei containing condensed chromatin suggestive of degeneration. In an additional set of cells transfected with pHIV-CAT+pwtΔ, stimulated and receiving antibody, soluble CD4 was added (FIG. 10F). Prominent syncytium with multiple nuclei containing prominent angulated nucleoli and vacuolated cytoplasm.

These data indicate that the addition of constructs that can generate antisense RNA encoding chemokine-like proteins to a HeLa cell line that expressed the HIV proteins HIV-1 proteins, Gag, Env, Tat, Rev, and Nef, but no reverse transcriptase, resulted in cell degeneration and death. Additional expression of gp120 increased the effect indicating that gp120 may be acting in association with the chemokine-like protein. These results further indicate that a chemokine-like protein is produced from the antisense RNA transcribed off of the antisense initiator in HIV.

Example 8

This embodiment illustrates that a recombinant HIV chemokine encoded by a nucleotide sequence according to the present invention can be purified from the host cell expression system using an affinity molecule such as by affinity chromatography. Also this embodiment illustrates using an affinity molecule to purify HIV chemokine from cells infected with HIV. An affinity molecule is a molecule that has binding specificity to the recombinant HIV chemokine or HIV chemokine from infected cells. Such an affinity molecule may be selected from the group consisting of a chemokine receptor (e.g., CCR5, CCR3, CCR2b, and CXCR4) or anti-HIV chemokine antisera (polyclonal or monoclonal, or anti-peptide HIV chemokine antisera). In one illustration, the recombinant HIV chemokine or HIV chemokine may be purified from a culture of transfected or infected human cells. The cultured cells are lysed, cellular debris is removed by centrifugation, and the supernatant is then applied to an affinity column. The column is washed, and then the recombinant HIV chemokine or HIV chemokine is eluted from the immobilized affinity molecule using methods known in the art. The purified recombinant CXC or HIV chemokine preparation may then be checked for purity by sodium dodecyl sulfate polyacrylamide gel electrophoresis; and for activity by a binding assay. Alternatively, peptides derived from the HIV chemokine sequence can be linked to an affinity matrix (i.e. CNBr activated sepharose) and used to purify chemokine peptide-specific antibody for use in isolation and detection.

Example 9

This embodiment illustrates that a monoclonal antibody (MAb) can be generated to epitopes specific for an HIV chemokine. Monoclonal antibodies to HIV chemokine may be developed using methods known in the art. For example, a method for making monoclonal antibodies immunoreactive with HIV chemokine involves the use of isolated and purified HIV chemokine as the immunogen; and an immunologically effective amount of the immunogen is used to immunize an animal (such as BALB/c mice) at timed intervals. A few days following the last immunization, spleens from the immunized animal are harvested aseptically, and placed into a tissue culture dish containing tissue culture medium. The primed spleen cells containing B-lymphocytes are mixed with a immunoglobulin non-secreting plasmacytoma cell line (usually a 10:1 to 1:1 ratio) for fusion. Fusion can be accomplished by methods including contacting the cells with a fusion agent such as polyethylene glycol (1 ml of a 50% solution, MW 1400) or by electrofusion. The cells from the fusion are then cloned out in microtiter plate wells. Typically, the plasmacytoma cell line is deficient in an enzyme such as hypoxanthine guanine phospho-ribosyl transferase such that fused hybridomas can be selected for by using a tissue culture selection medium such as a medium containing hypoxanthine, aminopterin, and thymidine. The hybridoma cultures are then incubated for several days, under standard tissue culture conditions, before the supernatants are tested for immunoreactivity to isolated and purified HIV chemokine. Alternatively, using methods standard in the art, human monoclonal antibodies may be made to an HIV chemokine (see. e.g., Ludwig et al, 1994, Cell. Imm.; Kanki and Takeuchi, 1995, Hum. Antibodies Hybridomas 6:89-92; Satoh et al., 1995, Immunol. Lett. 47:113-19; Vollmers et al., 1995, Cancer 76:550-558).

Murine monoclonals can be modified (making them more "human compatible") for administration into an individual using techniques standard in the art (e.g., as reviewed by Adair, 1992, Immunological Reviews 130: 6-37, herein incorporated by reference). For example, murine monoclonal antibodies may be "humanized" by replacing portions of the murine monoclonal antibody with the equivalent human sequence. In one embodiment, a chimeric antibody is constructed. The construction of chimeric antibodies is now a straightforward procedure (Adair, 1992, supra, at p. 13) in which the chimeric antibody is made by joining the murine variable region to a human constant region. Additionally, chimeric antibodies may be made by joining the hypervariable regions of the murine monoclonal antibody to human constant regions and parts of human variable regions using one of several techniques known in the art. Techniques for constructing chimeric antibodies (murine-human) of therapeutic potential have been described previously (see, e.g., Morrison et al., 1984, Proc. Natl. Acad. Sci. 81:6851-6855; Larrick et al., 1991, Hum. Antibod. Hybridomas 2:172-189; herein incorporated by reference). Thus, in one embodiment of the present invention, and using methods known in the art, the murine variable region of the monoclonal antibody to HIV chemokine according to the present invention is joined to a human constant region to form a chimeric anti-HIV chemokine monoclonal antibody having the same specificity as the anti-HIV chemokine MAb. In general, humanizing an murine MAb such as by making a chimeric antibody limits the development of human anti-mouse antibody responses. Additionally, the humanized antibodies generally change the pharmacokinetics by providing a longer half-life of such antibody, as compared to the half-life of murine antibody.

A chimeric MAb can also be constructed using a standard combination of techniques including polymerase chain reaction (PCR) cloning of antibody variable regions, the use of suitable expression vectors already containing the DNA encoding human constant region, insertion of the DNA for the murine MAb variable region into such vector in forming a recombinant vector, and expression of the resultant chimeric antibody by an expression system containing the recombinant vector (See, e.g., Daugherty et al., 1991, Nucl. Acids Res. 19:2471-2476; Maeda et al., 1991, Human Antibodies and Hybridomas 2:124-134; herein incorporated by reference). One expression vector can be used in which the vector is constructed so that the variable region and constant region genes are in tandem. Expression systems known to those skilled in the art for production of antibody or antibody fragments include mammalian cells (e.g. cell lines such as COS, NSO, or CHO), phage expression libraries, *Escherichia coli*, and yeast (Adair, 1992, supra). Any one of these monoclonal antibodies (purified human antibodies or purified, chimeric monoclonal antibodies) may then be tested for their ability to interact with HIV chemokine in binding assays.

Anti-HIV chemokine antibodies may also be used in competitive drug screening assays to identify compounds that function to bind HIV chemokine thereby neutralizing one or more functional activities of HIV chemokine (e.g., chemotaxis, and/or chemokine receptor binding). For example, a drug compound is tested for its ability to compete with neutralizing antibodies (capable of binding HIV chemokine) for binding to HIV chemokine. Selection of such possible drug compounds may also be facilitated by methods known in the art including determination of the three-dimensional structure of HIV chemokine (e.g., x-ray crystallography and/or computer modeling).

Example 10

This Example illustrates the use of HIV chemokine or antibodies to HIV chemokine for use in diagnostic assays. HIV chemokine, isolated according to the method of the present invention, or peptides formed therefrom, can be used as an antigen for diagnostic assays. Alternatively, HIV chemokine, or peptides formed therefrom, can be used as immunogens for generating anti-HIV chemokine antisera of diagnostic value. Antigenic sites of a protein may vary in size but can consist of from about 7 to about 14 amino acids. Thus, a protein the size of HIV chemokine may contain several discrete antigenic epitopes. Using synthetic processes, peptides of at least 7 to 14 amino acids in size may be generated which contain antigenic epitopes of HIV chemokine. The peptides can be synthesized from the amino acid sequence of an HIV chemokine using one of the several methods of peptide synthesis known in the art including standard solid peptide synthesis using tertbutyl-oxycarbonyl amino acids (Mitchell et al., 1978, J. Org. Chem. 43:2845-2852); using 9-fluorenylmethyloxycarbonyl amino acids on a polyamide support (Dryland et al., 1986, J. Chem. So. Perkin Trans. I, 125-137); by pepscan synthesis (Geysen et al., 1987, J. Immunol. Methods 03:259; 1984, Proc. Natl. Acad. Sci. USA 81:3998); or by standard liquid phase peptide synthesis. Modification of the peptides, such as by deletion and substitution of amino acids (and including extensions and additions to amino acids) and in other ways, may be made so as to not substantially detract from the immunological properties of the peptide. In particular, the amino acid sequence of the peptide may be altered by replacing one or more amino acids with functionally equivalent amino acids resulting in an alteration which is silent in terms of an observed differences in the binding specificity of the peptide.

In one embodiment, purified HIV chemokine, or peptides formed therefrom, may be used as antigens in immunoassays for the detection of antisera present in the body fluid of an individual. The body fluids include, but are not limited to, blood (e.g., serum) and urine. A diagnostic assay utilizing as an antigen HIV chemokine or a peptide formed therefrom, includes any immunoassay known in the art including, but not limited to, radioimmunoassay, ELISA, "sandwich" assay, precipitin reaction, agglutination assay, fluorescent immunoassay, and chemiluminescence-based immunoassay. Thus, for example, HIV chemokine or a peptide formed therefrom may be used as an antigen in an ELISA in which the antigen is immobilized to a selected surface; followed by blocking of unbound areas of the surface; contacting the body fluid sample with the selected surface containing immobilized antigen; washing the surface to remove materials in the sample which are not bound to the antigen; and detection of any immune complexes present (e.g., antibody to HIV chemokine complexed to the antigen) with a detectable moiety, such as by adding protein A peroxidase with subsequent color development. Other detectable moieties, conjugates and/or substrates known to those skilled in the art of diagnostics may be used to detect immunocomplexes formed. Thus, a diagnostic kit may contain the isolated HIV chemokine, or peptide formed therefrom as the antigen; a means for facilitating contact between the sample to be analyzed and the antigen (e.g., for an ELISA, a microtiter plate or wells); and a means for detecting the presence of immunocomplexes formed.

In another embodiment of the invention, using antisera to epitopes of an HIV chemokine, the clinical sample is assayed for the presence of the antigen, i.e., HIV chemokine. This antisera may be used by contacting the clinical sample, and detecting the presence of immunocomplexes formed between the antisera and antigen that is present in the clinical sample. Thus, a diagnostic kit may contain the antibody generated to HIV chemokine epitopes; a means for facilitating contact between the clinical sample and the antibody; and a means for detecting the presence of immunocomplexes formed.

Example 11

This embodiment of the present invention is to provide HIV chemokines, peptides formed therefrom, or modified variant of HIV chemokines (separately or collectively referred to as "HIV chemokine immunogen") to be used as immunogens in a prophylactic and/or therapeutic vaccine for active immunization to protect against or treat infections caused by HIV. For vaccine development, an HIV chemokine comprising the immunogen may be purified from HIV infected cells, or comprise recombinant HIV chemokine, using the methods according to the present invention. The HIV chemokine immunogen is included as the relevant immunogenic material in the vaccine formulation, and in immunoeffective amounts, to induce an immune response. Many methods are known for the introduction of a vaccine formulation into the human to be vaccinated. These include, but are not limited to, intradermal, intramuscular, intraperitoneal, intravenous, subcutaneous, ocular, intranasal, and oral administration. As known to those skilled in the art, the vaccine may further comprise a physiological carrier such as a pharmaceutically acceptable solution, polymer or liposomes; and an adjuvant, or a combination thereof.

Various adjuvants are used in conjunction with vaccine formulations. The adjuvants aid in attaining a more durable and higher level of immunity using smaller amounts of vaccine antigen or fewer doses than if the vaccine antigen were administered alone. The adjuvant may act to stimulate the immune effector cells, as well as delay release and degradation/processing of the HIV chemokine immunogen to enhance immune recognition. Examples of adjuvants include incomplete Freund's adjuvant, Adjuvant 65 (containing peanut oil, mannide monooleate and aluminum monostearate), oil emulsions, glycolipid analogs, lipopeptides, Ribi adjuvant, the pluronic polyols, polyamines, Avridine, Quil A, saponin, MPL, QS-21, and mineral gels such as aluminum hydroxide, aluminum phosphate, etc.

Another embodiment of this mode of the invention involves peptides derived from HIV chemokine as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such an HIV chemokine-specific hapten liked to a carrier molecule may be the immunogen in a vaccine formulation. There are many such carriers known in the art including, but not limited to, keyhole limpet hemocyanin, bovine serum albumin, and diphtheria toxin cross-reactive mutant protein ("CRM"). Additionally, there are several methods known in the art for conjugating a peptide to a carrier. Such methods include, but are not limited to, the use of glutaraldehyde, or succinimidyl m-maleimidobenzoate, or 1-ethyl-3-(3-dimethyl-aminopropyl)carbodiimide, or the use of bromo-acetylated peptide (see, e.g. Robey et al., 1989, Anal. Biochem. 177:373-377).

In another embodiment, as an alternative to active immunization, such as where an individual is suffering from late stages of AIDS, immunization may be passive, i.e. immunization comprising administration of a therapeutically effective amount of purified human-compatible anti-HIV chemokine antibodies (e.g., chimeric or human compatible monoclonal antibodies).

Example 12

This Example illustrates methods of administration of HIV chemokine, peptides formed therefrom, or modified variant of HIV chemokine, as agonists or antagonists (separately or collectively referred to as "HIV chemokine therapeutic"). The HIV chemokine therapeutic may be formulated in a pharmaceutically acceptable, nontoxic, carrier. Pharmaceutically acceptable carriers are generally known to include aqueous solutions such as water, various phosphate buffers, various buffered salines, alcoholic/aqueous solutions, and emulsions or suspensions; wherein the ionic strength, pH, and other properties of the pharmaceutically acceptable carrier may be adjusted to maximize delivery and activity of the HIV chemokine therapeutic to that site. Regarding pH, generally a pH range of 6 to 8 is typically used. It will be appreciated by those skilled in the art that the carrier may comprise any suitable pharmaceutically acceptable liposome having incorporated therein an HIV chemokine therapeutic according to the present invention. Such liposomal compositions may be administered in any conventional mode for therapeutic treatment. The pharmaceutically acceptable carrier may additionally comprise an agent that may improve the solubility of the HIV chemokine therapeutic while not inhibiting the binding activity of the HIV chemokine therapeutic. Such an additional agent may include, but is not limited to, a low concentration (e.g. concentration of 0.1% or less) of a nonionic detergent.

Depending on the physiologic site to be treated, the health of the individual to be treated, and the nature of the formulation, the HIV chemokine therapeutic may be administered in any one of the standard methods known in the art for administration of therapeutic agents, including, but not limited to, topical, by injection (e.g., intravenously), aerosol spray, intranasal, transmucosal, transdermal, and orally (by administered pills or liquids). As appreciated by those skilled in the art, dosage and frequency of dosage of an HIV chemokine therapeutic will depend on multiple patient variables, including the severity of AIDS, age, weight, responsiveness to therapy, tolerance of therapeutic, and clearance rate of therapeutic.

Example 13

This example demonstrates that the HIV antisense protein (HAP gene) sequence when transcribed and translated produces a protein that is recognized by the serum of HIV positive patients, but not negative controls. As described more fully below, a eukaryotic recombinant vector was designed incorporating the HIV-1 antisense gene sequence (SEQ ID NO:27) linked operably to a DNA sequence encoding an amino acid sequence comprising the carboxyterminal immunogenic epitope FLAG sequence. This construct (a) enabled immunodetection of the recombinant protein translated from the HIV-1 antisense gene sequence linked to the epitope FLAG using FLAG-specific antibody, (b) enabled immunoaffinity-isolation of the HIV-1 recombinant protein linked to the FLAG epitope, and (c) demonstrated the use of alternate translational mechanisms for facilitating translation of the HIV-1 antisense gene through the carboxyterminal-FLAG amino acid sequence (Hopp, et al., U.S. Pat. No. 4,851,341).

The alternate translations required translation through to the carboxy-terminal FLAG. These alternate translation products are referred to as "HIV antisense protein(s)" (HIV-AS) or "HAP(s)" (SEQ ID NOs: 28 and 29). Translation beginning from the first AUG at bases 51-53 of SEQ ID NO:27 begins a 105 amino acid reading frame (not including the eight amino acid FLAG sequence) and requires a +1 ribosomal frameshift between the codons of amino acids 27-28 in SEQ ID NO:28, as well as a read-through of a stop codon at position 36 in SEQ ID NO:28.

Figure 11:
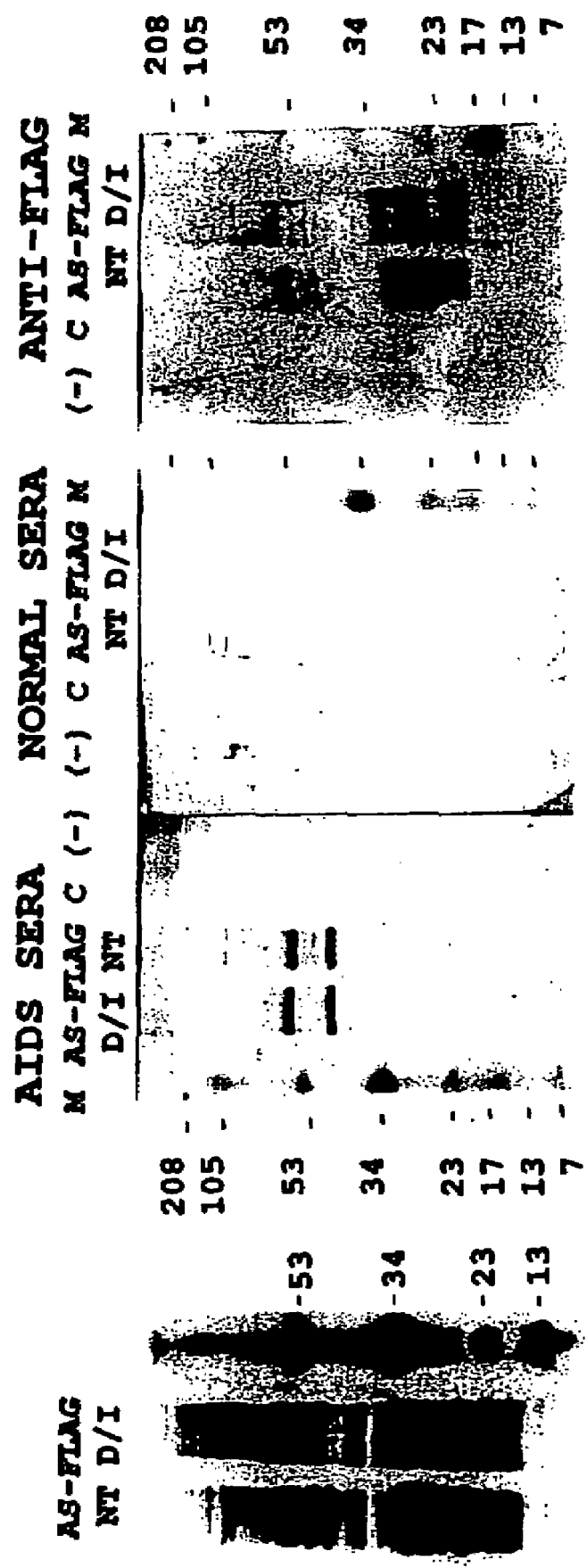
FIG. 11 shows through Western blotting that recombinant HIV-1 antisense protein is recognized by AIDS antisera as well as anti-FLAG antibody. (AS-FLAG)=affinity-purified proteins from HL2/3 cells transfected with HIV-AS-FLAG; (D/I)=treatment with DTT and Iodacetamide; (NT)=no treatment; (−) antisense gene insert in reverse orientation; C=control vector.

Translation could conceivably initiate at a CUG start codon at bases 44-46 in SEQ ID NO:27 (as has been described for human fibroblast growth factor 2) (Vagner, et al, 1995, Mol. Cell. Biol: 15, 35) and would require a read-through at positions 7 and 39 in SEQ ID NO:29. Either translation would generate protein ending in the reading frame that is in frame with the HIV-AS-FLAG carboxyterminal FLAG amino acid sequences which was detected by anti-FLAG antibody (FIG. 11).

Vector Construction

The expression vector which comprises SEQ ID NO:27 was constructed as follows. HIV-1 antisense gene sequences derived from pHIV-CAT (Nable et al., 1987, Nature 326: 711-713) were generated by PCR, gel-purified, and cloned into pTarget, as described by the manufacturer (Promega). The inserted sequences were digested with BamH1 (site contributed by pTarget) and EcoRV, gel purified, and directionally subcloned such that antisense gene sequences were operably linked into the pCMV-Tag4A vector (Stratagene) that had also been digested with BamH1 and EcoRV and gel-purified, using standard methods. The recombinant HIV antisense gene-FLAG vector contains the CMV immediate early promoter upstream of the HIV antisense gene sequence, but no translation start signal except that intrinsic to the HIV antisense gene as described above. In addition, the HIV antisense gene is linked to 9 amino acid sequences contributed by the vector in frame with the carboxy-terminal FLAG sequences and termination signals.

chemokines share related primary structure, particularly with a conserved motif of four cysteine residues. Early classification of chemokines was based on whether the first two cysteines are adjacent to each other ("CC chemokines"), or are separated by one amino acid ("CXC chemokines"). More recently, chemokines with a single "C" motif (for example lymphotactin) and "CXXXC" motif have been described. The α-chemokine receptor CXCR4 has been identified as a coreceptor required for HIV entry. The only known natural ligand for CXCR4 has been identified as the CXC chemokine SDF-1. SDF-1 has been shown to inhibit infection of CXCR4 and CD4 expressing cells by T-tropic HIV-1 strains (Oberlin et al., 1996, Nature 382:833-835). Thus, modified versions of chemokines are being tested to determine whether they may be used to block chemokine receptors from binding by HIV.

Importantly, this antisense gene insertion is in the opposite direction from what is known in the art for making recombinant HIV sequence containing vectors, such as LTR-CAT (Nable et al., 1987), and unexpectedly can result in translation through stop codons and shifted reading frames through the FLAG sequence, as demonstrated in FIG. 11. SEQ ID NO:27, only reversed within the vector (lanes "(–)", FIG. 11), and a vector control (lanes "C", FIG. 11) served as controls in transfection experiments, and did not produce recombinant proteins (FIG. 11). Transfection experiments and immunoanalysis for FIG. 11 is as described below.

Transfection Experiments

HL2/3 cells (Ciminale, et al., 1990, supra, obtained from the NIH AIDS Research and Reference Reagent Program) were grown to near confluency in 100 mm plates (~8×10$^6$ cells) and transfected with either the recombinant HIV-1 antisense gene-FLAG vector (HIV-AS-FLAG); or a negative control vector (–); or a luciferase-FLAG vector as a positive control using Transfectam, as described by the manufacturer (Promega). Following transfection and incubation for 2 hr, complete media consisting of DMEM/F12 (Gibco BRL), 10% fetal calf serum, penicillin-streptomycin, 1× nonessential amino acids and anti-PPLO (Gibco BRL) was added, along with Ca ionophore (50 ng/ml) and phorbol myristate acetate (PMA, 50 ng/ml), and the transfected cells were incubated overnight at 37° C. in 5% CO2. Cells were washed in Tris-buffered saline supplemented with 1 mM CaCl$_2$, and lysed with 1 ml lysis buffer per dish. Lysis buffer contained 25 mM Tris pH 7.4, 150 mM NaCl, 1 mM CaCl$_2$, 1% Triton X-100, 27 µg/mL aprotinin, 10 µg/mL leupeptin, and 100 mM PMSF. Following incubation on ice for 30 min, cells were scraped, transferred to microtubes and spun at 15,400×g to pellet cell debris. The cleared lysates from each set of transfections were purified over individual anti-FLAG M2 affinity columns, and eluted with 0.1M glycine (pH 3.5), per the manufacturer (Sigma). Pooled eluates were concentrated in dialysis tubing (MWCO=500) by packing in PEG 8000, and were then analyzed on denaturing Tris-tricine-urea PAGE gels (Schagger et al., 1987, Analytical Biochem. 166: 368-369).

Immunological Analysis

Gels were electroblotted onto nitrocellulose using an X cell II blot module (Novex), and the blots were blocked in either 1% BSA (for anti-FLAG Ab detection) or 5% non-fat dried milk/1% BSA, then probed with either biotinylated anti-FLAG M2 antibody (Stratagene), or alternatively, HIV-Ig (antisera) (AIDS Research and Reference Reagent Program, Division of AIDS, NIAID, NIH) or normal sera, followed by incubation with biotinylated anti-human immunoglobulin. This was then followed with colorimetric detection, as described (Ludwig, supra). FIG. 11 illustrates protein(s) that are isolated following anti-FLAG affinity purification of lysates from cells that had been transfected with the HIV-1 antisense gene-FLAG recombinant vector (AS-FLAG). The concentrated protein eluates were also analyzed for FLAG or HIV-specific epitopes by Western blot. The identical samples of PEG-concentrated, immunoaffinity-purified protein obtained from HIV-AS-FLAG transfected cells were split and reduced and alkylated (D/I) or not treated further (NT) and then analyzed in quadriplicate with denaturing SDS-PAGE gels. The replicate gels were either silver stained directly (panel A) or subjected to Western blotting for subsequent immunodetection (panels B-D) (FIG. 11). The blots were probed with anti-FLAG M2 Ab for FLAG epitopes ("Anti-FLAG"); or with either Ig purified from the sera of AIDS patients (panel B—"AIDS sera") or normal patients (panel C—"normal sera"), as indicated, to distinguish HIV-specific epitopes in the protein.

Because the expected molecular mass of this recombinant HIV-AS-FLAG protein is ≈13.6 kDa; a dimer, trimer and tetramer would be expected to be ≈27.2, 40.8 and 54.4, respectively. Similar molecular weight species are present and could represent a multimer of the recombinant protein or alternatively the recombinant protein tightly associated with another cellular (or HIV) protein, and are detected by anti-FLAG Ab (~27 and 54 mol wt. bands) or AIDS antisera (~40 and 54 mol wt. bands), but not normal sera. The 13.6 mol. wt. species was the faintest band by silver staining (panel A) and was not detected on Western blotting. Anti-FLAG affinity isolation was responsible for bringing down the recombinant protein and/or tightly associated proteins that bound to the recombinant protein from the cell lysates. This is confirmed by the complete absence of protein bands isolated (with the same affinity matrix) using lysates from negative control HL2/3 cells, which were either mock transfected, or transfected with a negative control vector with the antisense gene sequence reversed (−).

Example 14

Figure 12:
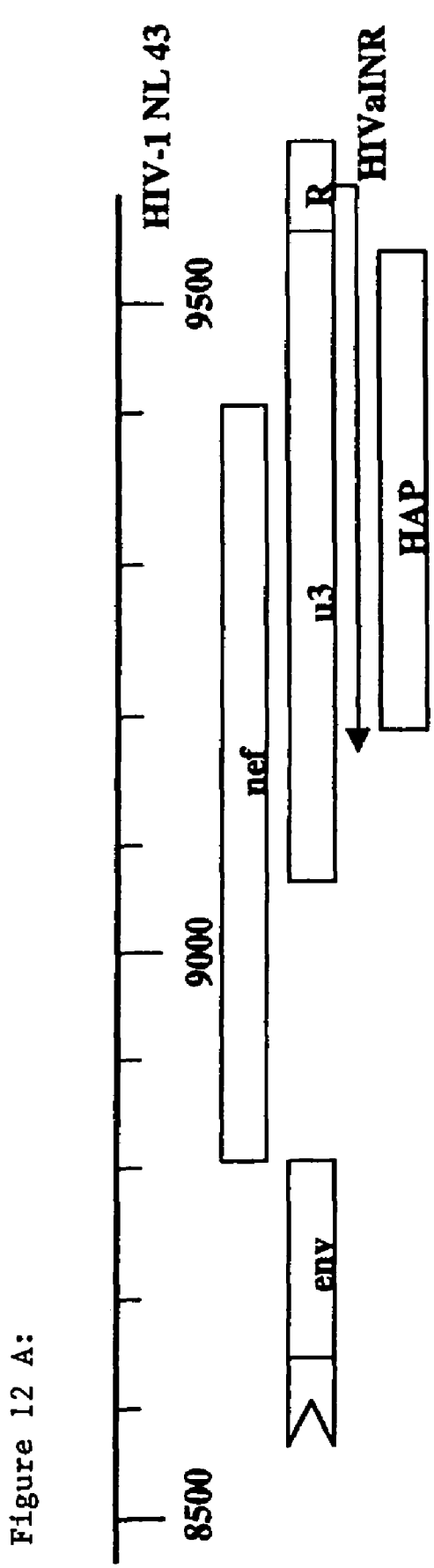
FIG. 12 is a diagramatic sequence alignment of reqions of HIV and similar sequences wherein alterations such as deletions can affect the survival rate of HIV positive individuals.

An example illustrative of this HIV antisense gene and its several antisense RNA and protein products (HAPs and chemokine-like proteins) role in HIV-1 disease progression is provided by several studies of long-term survivors (LTS) who are infected with an attenuated virus (FIG. 12 and SEQ ID NO:33). Some individuals, despite infection with HIV-1, have not progressed to the symptoms of AIDS over a prolonged period of time. These individuals have been variously termed long-term non-progressors (LTNPs) or long-term survivors (LTS), and are believed to provide important clues with respect to either altered host susceptibility or defenses, or specific viral gene defects that lead to viral attenuation and thereby enable prolonged survival of the human host. A number of groups have described attenuated virus isolated from LTNPs with deletions or mutations in nef gene sequences (FIG. 12) (Deacon et al., 1995, Science 270, 988-991; Kirchhoff et al., 1995, N. Engl. J. Med. 332, 228-232; Klein et al., 1995, J. Exp. Med. 181, 1365-1372; Mariani et al., 1996, J. Virol. 70, 7752-7764; Salvi et al., 1998, J. Virol. 72, 3646-3657). A particular group of LTNPs, the Sydney Blood Bank Cohort (SBBC), has provided an opportunity to study the long-term immunological consequences of infection with an attenuated HIV-1. Deacon, 1995, Dyer, et al J. Virol. 73, 436-443 (1999), Dyer, et al AIDS 11, 1565-1574 (1997), Greenway, et al AIDS 12, 555-561 (1998). The SBBC is a unique model of live attenuated vaccination in humans, in that all seven individuals were infected, through a single donor, with an attenuated HIV-1 containing deletions in nef and LTR (see FIG. 12; D36, C18, C98, C54-2), and many have had low levels of plasma viremia for up to 17 years following infection. In addition to strong HIV-specific cytotoxic T lymphocyte (CTL) responses in four of seven patients, serological studies of SBBC members showed nef-specific antibody reactivity to all nef overlapping peptides except one (aa 162-177), which corresponds to the consensus (and probably original) nef deletion (Dyer, et al AIDS 11, 1565-1574 (1997), Greenway, et al AIDS 12, 555-561 (1998). Studies of the SBBC suggests that the genomic deletions have increased in size over time, a finding that has been reported in another LTNP with an attenuated virus with a nef deletion (Deacon, 1995, Kirchhoff, 1995, Greenway, 1998). Defects in NFkb and Sp1 sites were observed in a subset of LTNPs in yet another study (Salvi et al, J. Virol. 72, 3646-3657). This region of specific nef/LTR gene sequences deleted or mutated in these studies of LTS/LTNPs also corresponds to defects in the HIV antisense gene or its protein product (HAP), as illustrated in FIG. 12.

Additional evidence that an intact HIV-1 proviral DNA encoding the HAP proteins, which partially overlaps nef in the opposite orientation, is required for progression to AIDS was provided by a mouse transgenic model. The HIV-1 nef/LTR transgene (which contains the HAP gene) in mice induced a dominant severe immunodeficiency (without the expected evidence of nef protein expression) (FIG. 12D: Mouse Transgene associated with severe immunodeficiency (Lindemann et al, 1994, J. Exp. Med. 179, 797-806). The presence of a HIV-1 nef/3' LTR transgene in mice was associated with the development of a dominant severe immunodeficiency that included loss of CD4+CD8+ and CD4+CD8− thymocytes at early stages of ontogeny, as well as a severe depletion and functional impairment of peripheral T cells (FIG. 12D). The transgenic mice from a specific line, B6/338L, showed a defective immune response to several viral infections and a high mortality rate, and also eventually developed lymphadenopathy and splenomegaly. Within this transgenic mouse line (B6/338L), the single-copy transgene that integrated also demonstrated a rearrangement of the original injected construct. The integrated transgene contained 1.5 kb of HIV-1 sequence that included nef and the entire LTR (and therefore the previously unrecognized HAP gene) linked to a mouse TCR □ chain promoter, but these were rearranged upstream from the mTCR □ enhancer regulatory control elements (FIG. 12D). Interestingly, while these profound phenotypic and functional immune impairments were convincingly demonstrated associated with the presence of the nef/LTR transgene, no Nef protein expression could be detected (Lindemann et al, J. Exp. Med. 179, 797-806). These LTS truncated HAP protein products may provide a safer alternative for immunization with DNA vaccines or proteins (FIG. 12 and Sequence ID 33).

Example 15

As an additional embodiment, a eukaryotic recombinant vector incorporating features enabling expression in human cells, and containing the HIV-1 antisense gene sequences operably linked to enable efficient expression of RNA and protein in human cells would form the basis of a DNA-vaccine that expresses HAP protein(s) or peptides (DNA-HAP). For instance, a less pathogenic alternative to using an attenuated virus as a vaccine, would be the development of a DNA vaccine that includes elements that enable HAP protein or HAP peptide expression, as well as recruitment of antigen-presenting cells such as dendritic cells, for efficient HAP antigenic determinant presentation to human T cells.

It may be important not to target the human T cell directly (as the intact HIV does), but instead employ mechanisms that allow the antigen-presenting cells or dendritic cells (DC) to take up the DNA-HAP, translate the protein, and then process it into peptides for antigen presentation on the DC cell surface. Vaccination with a plasmid encoding a viral protein, rather than the recombinant protein or peptide directly, has the advantage of allowing the appropriate post-translational modifications and cellular sorting to occur, along with allowing a variety of protein antigenic determinants to be selected for MHC presentation.

A further advantage of DNA vaccines is that the host is not exposed to a live replicating vector, or an attenuated version of the pathogen, which, as in the case of attenuated SIV/HIV, may prove deadly. Various techniques known to those skilled in the art may be utilized to enhance the immunogenicity of the DNA vaccine such that it begins to provide the level of protection found with live replicating vector or attenuated virus. Furthermore, dendritic cells (DC) may be superior antigen presenting cells for primary immune responses in vitro and in vivo (Young and Inaba, 1996, J. Exp. Med. 183: 7-11), and it was recently shown that enhanced protective immunity was incurred by immunization IM with DCs that had been transfected in vitro with DNA encoding viral antigens (Manickan, et al., 1997, J. Leukoc. Biol. 61: 125-132). However, it may be more practical to target delivery of the DNA vaccine to DCs in vivo or to utilize strategies that recruit DCs (Xiang and Ertl, 1995, Immunity 2: 129-135). A vector comprising SEQ ID NO:27 contains many of the required elements of vectors for vaccine use: 1; a strong enhancer-promoter (human cytomegalovirus immediate/early promoter), 2; mRNA transcript termination/polyadenylation sequences, 3; an intron, and 4; an origin of replication and an antibiotic resistance gene to allow growth of plasmid in *E. coli* for ease of production of large quantities of vaccine.

Example 16

From the teaching of the present invention, the genetic code of the HAP gene(s) for individual HIV subtypes can be inferred from an examination of the whole genome alignments presented in the literature (ie HIV Sequence Compendium 2000, Kuiken C. et al, Los Alamos National Laboratory). While this compendium includes with the subtype gene sequence alignments the HIV protein sequences of the HIV-1 Gag, Pol, Env, Tat, Rev, Vif Vpr, Vpu, and Nef genes (all with mRNAs oriented in the sense direction), it is important to note that no protein sequences are annotated from genes oriented in the opposite direction and translated from antisense RNA as are the HAP genes presented herein. Thus, the HAP gene(s) are unique and not recognized previously.

As an additional example, SEQ ID NO:31 demonstrates the HAP amino acid sequence translated from the consensus A sequences (SEQ ID NO:32) and originating from a variant HIVaINR (U.S. Pat. No. 5,919,677). This A subtype HAP amino acid sequence contains 12 of 17 amino acids at the start of the protein which are identical to the start of SEQ ID NO:28. In addition, between aa 52-106, SEQ ID NO:31 contains an amino acid sequence identical in 35/54 positions to sequence SEQ ID NO:28. The A subtype contains some species with a Trp instead of a stop at position 107, and continues to a stop at position 153, illustrated in sequence SEQ ID NO:31. As a further example, subtype C protein sequences for HAP (SEQ ID NO:35) originating off the HIVaINR (U.S. Pat. No. 5,919,677) which produces RNA of SEQ ID NO:34 also contains 14 identical of the first 17 amino acids (as compared to SEQ ID NO:28), and 44 of 56 amino acids identical between aa 50-105 (corresponding to SEQ ID NO:28 aa 50-105). The C subtype also contains variants with a Trp at position 106 instead of a stop.

The long-term survivor HAP variant (SEQ ID NO:33), despite the presence of genomic deletions and a region of sequence duplication as compared to the whole genome alignments, contains the first 17 amino acids identical to the first 17 aa of SEQ ID NO:28. The LTS carboxyterminal sequence of SEQ ID NO:33 (aa 80/81-90) also contains sequence identical to the A subtype (SEQ ID NO:31 aa 143-152) and C subtype (SEQ ID NO:35 aa 141-149.)

A peptide (SEQ ID NO:36) corresponding to a portion of the HAP protein of SEQ ID NO:28 (amino acids 40-51) and SEQ ID NO:29 (amino acids 43-54) was used to raise antibodies in rabbits.

Having described the preferred embodiments of the present invention, it will be apparent to one of ordinary skill in the art that various modifications may be made to the disclosed embodiments, and that such modifications are intended to be within the scope of the present invention.

What is claimed is:

1. An isolated protein having the sequence of SEQ ID No: 28 except that the protein has a substitution selected from the group consisting of: His replaced by Asp at position 3; Arg replaced by His at position 16; Ala replaced by Val at position 23; Asn replaced by Arg or Ser at position 28; Asn replaced by Ser at position 33; Pro replaced by Leu at position 45; Arg replaced by Cys at position 46; Thr replaced by Ile at position 59; Ser replaced by Pro at position 62; Gln replaced by Pro or Leu at position 63; Gly replaced by His at position 64; His replaced by Pro at position 65; Phe replaced by Ser at position 67; Gln replaced by Trp at position 72; Trp replaced by Cys at position 77; Tyr replaced by His at position 82; Pro replaced by Ser at position 87; Tyr replaced by Ala at position 88; Ala replaced by Thr at position 95, and combinations thereof.

2. An isolated protein having the sequence of SEQ ID NO:28.

3. An isolated antibody that binds to the protein of claim 1.

4. An isolated antibody that binds to the protein of claim 2.

* * * * *

SEQUENCE LISTING

```
<160> NUMBER OF SEQ ID NOS: 36

<210> SEQ ID NO 1
<211> LENGTH: 540
<212> TYPE: DNA
<213> ORGANISM: Human immunodeficiency virus
```

-continued

<220> FEATURE:
<221> NAME/KEY: misc_feature
<223> OTHER INFORMATION: dsDNA intermediate of lbl revINRold
(Note: antisense gene of negative polarity
with respect to HIV-1 usual coding region)

<400> SEQUENCE: 1
aggcaagctt tattgaggct taagcagtgg gttccctagt tagccagaga gctcccaggc 60
tcagatctgg tctaaccaga gagacccagt acaggcaaaa agcagctgct tatatgtagc 120
atctgagggc tcgccactcc ccagtcccgc ccaggccaca cctccctgga aagtccccag 180
cggaaagtcc cttgtagaaa gctcgatgtc agcagtcttt gtagtactcc ggatgcagct 240
ctcgggccat gtgacgaaat gctaggaggc tgtcaaactt ccacactaat acttctccct 300
ccgggtcctc catcccatgc tggctcatag ggtgtaacaa gctgttcttc tctccttatt 360
tggcctcttc tacttgctct ggttcaactg gtactaactt gaagcaccat ccaaaggtca 420
gtggatatct gatccctggc cctggtgtgt agttctgcca atcagggaag tagccttgtg 480
tgtggtagat ccacagatca aggatctctt gtctttttg ggaccaaatt agcccttcca 540

<210> SEQ ID NO 2
<211> LENGTH: 81
<212> TYPE: PRT
<213> ORGANISM: Human immunodeficiency virus
<220> FEATURE:
<221> NAME/KEY: misc_feature
<223> OTHER INFORMATION: HIV chemokine protein from lbl revINRold

<400> SEQUENCE: 2

Met Ser Ala Val Phe Val Val Leu Arg Met Gln Leu Ser Gly His Val
1 5 10 15

Thr Lys Cys Arg Arg Leu Ser Asn Phe His Thr Asn Thr Ser Pro Ser
20 25 30

Gly Ser Ser Ile Pro Cys Trp Leu Ile Gly Cys Asn Lys Leu Phe Phe
35 40 45

Ser Pro Tyr Leu Ala Ser Ser Thr Cys Ser Gly Ser Thr Gly Thr Asn
50 55 60

Leu Lys His His Pro Leu Val Ser Gly Tyr Leu Ile Pro Gly Pro Gly
65 70 75 80

Val

<210> SEQ ID NO 3
<211> LENGTH: 22
<212> TYPE: DNA
<213> ORGANISM: Human immunodeficiency virus
<220> FEATURE:
<221> NAME/KEY: misc_feature
<223> OTHER INFORMATION: 5' sense primer

<400> SEQUENCE: 3
tttcgtcaca tggcccgagc gc 22

<210> SEQ ID NO 4
<211> LENGTH: 25
<212> TYPE: DNA
<213> ORGANISM: Human immunodeficiency virus
<220> FEATURE:
<221> NAME/KEY: misc_feature
<223> OTHER INFORMATION: 3' antisense primer

<400> SEQUENCE: 4
ccagagagac ccagtacagg caaaa 25

<210> SEQ ID NO 5
<211> LENGTH: 20
<212> TYPE: DNA
<213> ORGANISM: Human immunodeficiency virus
<220> FEATURE:
<221> NAME/KEY: misc_feature
<223> OTHER INFORMATION: 3' Mae I antisense primer

<400> SEQUENCE: 5
ttccctagtt agccagagag                                               20

<210> SEQ ID NO 6
<211> LENGTH: 390
<212> TYPE: RNA
<213> ORGANISM: Human immunodeficiency virus
<220> FEATURE:
<221> NAME/KEY: misc_feature
<223> OTHER INFORMATION: antisense RNA originating off HIVaINR
      in SF2 HIV strain

<400> SEQUENCE: 6
agaucugguc uaaccagaga gacccaguac aggcaaaaag cagcugcuua uaugcagcau    60
cugagggcac gccacucccc agucccgccc aggccacgcc uccuggaaa guccccagcg   120 gaaagucccu guagaaagc ucgaugucag cagucuuugu aguaccucgg augcagcucu   180
cgggccaugu gaugaaaugc uaguuugcug ucaaaccucc acacuaacac uucuuucucc   240
gcguccucca ucccaugcag gcucauaggg uguaacaagc uguuguucuc uccuucauug   300
gccucuucua ccuucucugg cucaacuggu acuagcuuga agcaccaucc aaaggucagu   360
ggauaucuga ucccuggccc uggugugu ag                                   390

<210> SEQ ID NO 7
<211> LENGTH: 112
<212> TYPE: PRT
<213> ORGANISM: Human immunodeficiency virus
<220> FEATURE:
<221> NAME/KEY: misc_feature
<223> OTHER INFORMATION: HIV chemokine protein (1st start site:
      (+1) ribosomal frameshift at nucleotide 133; and
      (-1) ribosomal frameshift at nucleotide 265)
      from SF2 HIV

<400> SEQUENCE: 7

Met Gln His Leu Arg Ala Arg His Ser Pro Val Pro Pro Arg Pro Arg
1               5                   10                  15

Leu Pro Gly Lys Ser Pro Ala Glu Ser Pro Leu Arg Lys Leu Asp Val
            20                  25                  30

Ser Ser Leu Cys Ser Thr Pro Asp Ala Ala Leu Gly Pro Cys Asp Glu
        35                  40                  45

Met Leu Val Cys Cys Gln Thr Ser Thr Leu Thr Leu Leu Ser Pro Arg
    50                  55                  60

Pro Pro Ser His Ala Gly Ser Ile Gly Cys Asn Lys Leu Leu Phe Ser
65                  70                  75                  80

Pro Ser Leu Ala Ser Ser Thr Phe Ser Gly Ser Thr Gly Thr Ser Leu
                85                  90                  95

Lys His His Pro Lys Val Ser Gly Tyr Leu Ile Pro Gly Pro Gly Val
            100                 105                 110

<210> SEQ ID NO 8
<211> LENGTH: 82
<212> TYPE: PRT

```
<213> ORGANISM: Human immunodeficiency virus
<220> FEATURE:
<221> NAME/KEY: misc_feature
<223> OTHER INFORMATION: HIV chemokine protein (2nd start site:
      (-1) ribosomal frameshifts at nucleotides 200 and 265)
      from SF2 HIV

<400> SEQUENCE: 8

Met Ser Ala Val Phe Val Val Leu Arg Met Gln Leu Ser Gly His Val
1               5                   10                  15

Met Lys Cys Leu Val Cys Cys Gln Thr Ser Thr Leu Thr Leu Leu Ser
                20                  25                  30

Pro Arg Pro Pro Ser His Ala Gly Ser Ile Gly Cys Asn Lys Leu Leu
            35                  40                  45

Phe Ser Pro Ser Leu Ala Ser Ser Thr Phe Ser Gly Ser Thr Gly Thr
        50                  55                  60

Ser Leu Lys His His Pro Lys Val Ser Gly Tyr Leu Ile Pro Gly Pro
65                  70                  75                  80

Gly Val

<210> SEQ ID NO 9
<211> LENGTH: 81
<212> TYPE: PRT
<213> ORGANISM: Human immunodeficiency virus
<220> FEATURE:
<221> NAME/KEY: misc_feature
<223> OTHER INFORMATION: HIV chemokine protein (2nd start site:
      (+1) ribosomal frameshift at nucleotide 201)
      from SF2 HIV

<400> SEQUENCE: 9

Met Ser Ala Val Phe Val Val Leu Arg Met Gln Leu Ser Gly His Val
1               5                   10                  15

Met Lys Cys Ser Leu Leu Ser Asn Leu His Thr Asn Thr Ser Phe Ser
                20                  25                  30

Ala Ser Ser Ile Pro Cys Arg Leu Ile Gly Cys Asn Lys Leu Leu Phe
            35                  40                  45

Ser Pro Ser Leu Ala Ser Ser Thr Phe Ser Gly Ser Thr Gly Thr Ser
        50                  55                  60

Leu Lys His His Pro Lys Val Ser Gly Tyr Leu Ile Pro Gly Pro Gly
65                  70                  75                  80

Val

<210> SEQ ID NO 10
<211> LENGTH: 112
<212> TYPE: PRT
<213> ORGANISM: Human immunodeficiency virus
<220> FEATURE:
<221> NAME/KEY: misc_feature
<223> OTHER INFORMATION: HIV chemokine protein (1st start site at
      nucleotide 52; (+1) ribosomal frameshift at
      nucleotide 133, (-1) ribosomal frameshift at
      nucleotide 265) from (Pt) CNS HIV

<400> SEQUENCE: 10

Met Gln His Leu Arg Ala Arg His Ser Pro Val Pro Pro Arg Pro His
1               5                   10                  15

Leu Pro Gly Lys Ser Pro Ala Glu Ser Pro Leu Arg Lys Phe Asp Val
                20                  25                  30

Ile Ser Ser Cys Ser Thr Pro Asp Ala Ala Leu Gly Pro Cys Gly Glu
            35                  40                  45
```

```
Met Leu Gly Cys Cys Gln Thr Ser Thr Leu Thr Leu Leu Ser Pro Gly
        50                  55                  60

Arg Pro Ser His Ala Gly Ser Ile Gly Cys Asn Ser Thr Leu Phe Ser
 65                  70                  75                  80

Pro Ser Leu Ala Ser Ser Ile Phe Ser Gly Ser Thr Gly Thr Ser Leu
                     85                  90                  95

Lys His His Pro Lys Val Ser Gly Tyr Leu Val Pro Gly Pro Gly Val
                100                 105                 110
```

<210> SEQ ID NO 11
<211> LENGTH: 112
<212> TYPE: PRT
<213> ORGANISM: Human immunodeficiency virus
<220> FEATURE:
<221> NAME/KEY: misc_feature
<223> OTHER INFORMATION: HIV chemokine protein (1st start site;
      (-1) ribosomal frameshift at nucleotide 133,
      (+1) ribosomal frameshift at 265),
      from (Pt)CNS HIV

<400> SEQUENCE: 11

```
Met Gln His Leu Arg Ala Arg His Ser Pro Val Pro Arg Pro Arg His
  1               5                  10                  15

Leu Pro Gly Lys Ser Pro Ala Glu Ser Pro Leu Val Glu Ser Ser Met
                 20                  25                  30

Ser Ser Val Leu Val Leu Arg Met Gln Leu Ser Gly Pro Val Val
            35                  40                  45

Lys Cys Arg Val Lys Ser Asn Phe His Thr Asn Thr Ser Leu Ser Gly
        50                  55                  60

Ser Ser Ile Pro Cys Arg Leu Ile Gly Cys Asn Asn Thr Leu Phe Ser
 65                  70                  75                  80

Pro Ser Leu Ala Ser Ser Ile Phe Ser Gly Ser Thr Gly Thr Ser Leu
                     85                  90                  95

Lys His His Pro Lys Val Ser Gly Tyr Leu Val Pro Gly Pro Gly Val
                100                 105                 110
```

<210> SEQ ID NO 12
<211> LENGTH: 117
<212> TYPE: PRT
<213> ORGANISM: Human immunodeficiency virus
<220> FEATURE:
<221> NAME/KEY: misc_feature
<223> OTHER INFORMATION: HIV chemokine protein (1st start site;
      (+1) ribosomal frameshift at nucleotide 133,
      (-1) ribosomal frameshift at nucleotide 280)
      from (Pt)LN/SP HIV

<400> SEQUENCE: 12

```
Met Gln His Leu Arg Ala Arg His Ser Pro Val Pro Ser Pro Arg
  1               5                  10                  15

Leu Pro Gly Lys Ser Pro Ala Glu Ser Pro Leu Arg Lys Leu Gly Val
                 20                  25                  30

Ser Ser Gly Gly Val Ser Ser Ser Cys Ser Ser Pro Asp Ala Ala Leu
            35                  40                  45

Gly Leu Arg Asp Glu Met Pro Gly Gly Cys Gln Thr Ser Thr Leu Arg
        50                  55                  60

Leu Leu Ser Lys Gly Arg Pro Ser His Ala Gly Ser Ile Gly Cys Asn
 65                  70                  75                  80

Arg Leu Leu Phe Ser Pro Ser Leu Ala Ser Ser Ile Phe Ser Ala Ser
                     85                  90                  95
```

```
Thr Gly Thr Ser Leu Lys His His Pro Lys Val Ser Gly Tyr Leu Ile
            100                 105                 110

Pro Gly Pro Gly Val
        115

<210> SEQ ID NO 13
<211> LENGTH: 118
<212> TYPE: PRT
<213> ORGANISM: Human immunodeficiency virus
<220> FEATURE:
<221> NAME/KEY: misc_feature
<223> OTHER INFORMATION: HIV chemokine protein (1st start site;
      (-1) ribosomal frameshift at nucleotide 133,
      (+1) ribosomal frameshift at nucleotide 280)
      from (Pt) LN/SP HIV

<400> SEQUENCE: 13

Met Gln His Leu Arg Ala Arg His Ser Pro Val Pro Pro Ser Pro Arg
1               5                   10                  15

Leu Pro Gly Lys Ser Pro Ala Glu Ser Pro Leu Val Glu Ser Ser Val
            20                  25                  30

Ser Ala Val Ser Met Ser Ala Val Leu Val Val Arg Met Gln Leu
            35                  40                  45

Ser Gly Tyr Val Met Lys Cys Gln Ala Ala Val Lys Pro Pro Leu Leu
    50                  55                  60

Arg Leu Leu Ser Leu Gly Pro Pro Ser His Ala Gly Ser Ile Gly Cys
65                  70                  75                  80

Asn Arg Leu Leu Phe Ser Pro Ser Leu Ala Ser Ser Thr Phe Ser Ala
                85                  90                  95

Ser Thr Gly Thr Ser Leu Lys His His Pro Lys Val Ser Gly Tyr Leu
            100                 105                 110

Ile Pro Gly Pro Gly Val
        115

<210> SEQ ID NO 14
<211> LENGTH: 112
<212> TYPE: PRT
<213> ORGANISM: Human immunodeficiency virus
<220> FEATURE:
<221> NAME/KEY: misc_feature
<223> OTHER INFORMATION: HIV chemokine protein (1st start site;
      (-1) ribosomal frameshift at nucleotide 133,
      (+1) ribosomal frameshift at nucleotide 265)
      from SF2 HIV

<400> SEQUENCE: 14

Met Gln His Leu Arg Ala Arg His Ser Pro Val Pro Pro Arg Pro Arg
1               5                   10                  15

Leu Pro Gly Lys Ser Pro Ala Glu Ser Pro Leu Val Glu Ser Ser Met
            20                  25                  30

Ser Ala Val Phe Val Val Leu Arg Met Gln Leu Ser Gly His Val Met
            35                  40                  45

Lys Cys Ser Leu Leu Ser Asn Leu His Thr Asn Thr Ser Phe Ser Ala
    50                  55                  60

Ser Ser Ile Pro Cys Arg Leu Ile Gly Cys Asn Lys Leu Leu Phe Ser
65                  70                  75                  80

Pro Ser Leu Ala Ser Ser Thr Phe Ser Gly Ser Thr Gly Thr Ser Leu
                85                  90                  95

Lys His His Pro Lys Val Ser Gly Tyr Leu Ile Pro Gly Pro Gly Val
            100                 105                 110
```

<210> SEQ ID NO 15
<211> LENGTH: 112
<212> TYPE: PRT
<213> ORGANISM: Human immunodeficiency virus
<220> FEATURE:
<221> NAME/KEY: misc_feature
<223> OTHER INFORMATION: HIV chemokine protein with read-through from SF2 HIV
<220> FEATURE:
<221> NAME/KEY: Xaa
<222> LOCATION: (28)..(28)
<223> OTHER INFORMATION: Xaa is any amino acid
<220> FEATURE:
<221> NAME/KEY: Xaa
<222> LOCATION: (37)..(37)
<223> OTHER INFORMATION: Xaa is any amino acid
<220> FEATURE:
<221> NAME/KEY: Xaa
<222> LOCATION: (47)..(47)
<223> OTHER INFORMATION: Xaa is any amino acid

<400> SEQUENCE: 15

Met Gln His Leu Arg Ala Arg His Ser Pro Val Pro Pro Arg Pro Arg
1               5                   10                  15

Leu Pro Gly Lys Ser Pro Ala Glu Ser Pro Leu Xaa Lys Ala Arg Cys
            20                  25                  30

Gln Gln Ser Leu Xaa Tyr Ser Gly Cys Ser Ser Arg Ala Met Xaa Ser
        35                  40                  45

Asn Ala Ser Leu Leu Ser Asn Leu His Thr Asn Thr Ser Phe Ser Ala
    50                  55                  60

Ser Ser Ile Pro Cys Arg Leu Ile Gly Lys Asn Lys Leu Leu Phe Ser
65                  70                  75                  80

Pro Ser Leu Ala Ser Ser Thr Phe Ser Gly Ser Thr Gly Thr Ser Leu
                85                  90                  95

Lys His His Pro Lys Val Ser Gly Tyr Leu Ile Pro Gly Pro Gly Val
            100                 105                 110

<210> SEQ ID NO 16
<211> LENGTH: 111
<212> TYPE: PRT
<213> ORGANISM: Human immunodeficiency virus
<220> FEATURE:
<221> NAME/KEY: misc_feature
<223> OTHER INFORMATION: HIV chemokine protein from YU2 strain with a (+1) and (-1) ribosomal frameshift

<400> SEQUENCE: 16

Met Gln His Leu Arg Ala Arg His Ser Pro Val Pro Pro Arg Pro Arg
1               5                   10                  15

Phe Pro Gly Lys Ser Pro Ala Glu Ser Pro Leu Arg Lys Leu Glu Val
            20                  25                  30

Ile Ser Ser Cys Ser Thr Pro Asp Ala Ala Leu Gly Pro Arg Asp Glu
        35                  40                  45

Met Leu Val Cys Cys Gln Thr Ser Thr Leu Thr Leu Leu Ser Pro Gly
    50                  55                  60

His Pro Phe His Ala Gly Ser Ile Gly Cys Asn Lys Gln Leu Phe Ser
65                  70                  75                  80

Pro Ala Leu Ala Ser Ser Ile Phe Ser Gly Ser Thr Gly Thr Ser Leu
                85                  90                  95

Lys His His Pro Lys Val Ser Gly His Leu Val Pro Pro Gly Val
            100                 105                 110

```
<210> SEQ ID NO 17
<211> LENGTH: 111
<212> TYPE: PRT
<213> ORGANISM: Human immunodeficiency virus
<220> FEATURE:
<221> NAME/KEY: misc_feature
<223> OTHER INFORMATION: HIV chemokine protein (1st start site;
      (-1) ribosomal frameshift at nucleotide 133,
      (+1) ribosomal frameshift at nucleotide 265)
      from YU2 HIV

<400> SEQUENCE: 17

Met Gln His Leu Arg Ala Arg His Ser Pro Val Pro Pro Arg Pro Arg
1               5                   10                  15

Phe Pro Gly Lys Ser Pro Ala Glu Ser Pro Leu Val Glu Ser Ser Arg
                20                  25                  30

Ser Ser Val Leu Val Leu Arg Met Gln Leu Ser Gly His Val Met
            35                  40                  45

Lys Cys Arg Arg Leu Ser Asn Leu His Ser Asn Pro Ser Leu Ser Gly
    50                  55                  60

Ser Ser Ile Pro Cys Trp Leu Ile Gly Cys Asn Lys Gln Leu Phe Ser
65                  70                  75                  80

Pro Ala Leu Ala Ser Ser Ile Phe Ser Gly Ser Thr Gly Thr Ser Leu
                85                  90                  95

Lys His His Pro Lys Val Ser Gly His Leu Val Pro Pro Gly Val
            100                 105                 110

<210> SEQ ID NO 18
<211> LENGTH: 111
<212> TYPE: PRT
<213> ORGANISM: Human immunodeficiency virus
<220> FEATURE:
<221> NAME/KEY: misc_feature
<223> OTHER INFORMATION: HIV chemokine protein with read-through
      from YU2 HIV
<220> FEATURE:
<221> NAME/KEY: Xaa
<222> LOCATION: (28)..(28)
<223> OTHER INFORMATION: Xaa is any amino acid.
<220> FEATURE:
<221> NAME/KEY: Xaa
<222> LOCATION: (37)..(37)
<223> OTHER INFORMATION: Xaa is any amino acid.
<220> FEATURE:
<221> NAME/KEY: Xaa
<222> LOCATION: (47)..(47)
<223> OTHER INFORMATION: Xaa is any amino acid.

<400> SEQUENCE: 18

Met Gln His Leu Arg Ala Arg His Ser Pro Val Pro Pro Arg Pro Arg
1               5                   10                  15

Phe Pro Gly Lys Ser Pro Ala Glu Ser Pro Leu Xaa Lys Ala Arg Gly
                20                  25                  30

His Gln Phe Leu Xaa Tyr Ser Gly Cys Ser Ser Arg Ala Thr Xaa Ser
            35                  40                  45

Asn Ala Arg Arg Leu Ser Asn Leu His Ser Asn Pro Ser Leu Ser Ala
    50                  55                  60

Ser Ser Ile Pro Cys Trp Leu Ile Gly Cys Asn Lys Gln Leu Phe Ser
65                  70                  75                  80

Pro Ala Leu Ala Ser Ser Ile Phe Ser Gly Ser Thr Gly Thr Ser Leu
                85                  90                  95

Lys His His Pro Lys Val Ser Gly His Leu Val Pro Pro Gly Val
            100                 105                 110
```

```
<210> SEQ ID NO 19
<211> LENGTH: 112
<212> TYPE: PRT
<213> ORGANISM: Human immunodeficiency virus
<220> FEATURE:
<221> NAME/KEY: misc_feature
<223> OTHER INFORMATION: HIV chemokine protein with read-through
      from ELI strain of HIV
<220> FEATURE:
<221> NAME/KEY: Xaa
<222> LOCATION: (28)..(28)
<223> OTHER INFORMATION: Xaa is any amino acid.
<220> FEATURE:
<221> NAME/KEY: Xaa
<222> LOCATION: (37)..(37)
<223> OTHER INFORMATION: Xaa is any amino acid.
<220> FEATURE:
<221> NAME/KEY: Xaa
<222> LOCATION: (97)..(97)
<223> OTHER INFORMATION: Xaa is any amino acid.

<400> SEQUENCE: 19

Met Gln His Leu Arg Val Ser His Ser Pro Val Pro Pro Ser Pro Arg
1               5                   10                  15

Leu Pro Gly Lys Ser Pro Ala Glu Ser Pro Leu Xaa Lys Ala Arg Cys
            20                  25                  30

His Gln Phe Leu Xaa Asn Ser Gly Cys Ile Ser Arg Ala Leu Cys Ser
        35                  40                  45

Asn Ala Ser Leu Leu Leu Asn Leu His Phe Asn Thr Cys Leu Ser Gly
    50                  55                  60

Ser Ser Ile Pro Cys Trp His Ile Gly Cys Asn Lys Leu Leu Val Ser
65                  70                  75                  80

Pro Ser Val Ser Ser Thr Ser Cys Gly Ser Thr Gly Thr Ser Ser
                85                  90                  95

Xaa His His Pro Lys Val Ser Gly Tyr Leu Ile Pro Gly Pro Gly Val
            100                 105                 110

<210> SEQ ID NO 20
<211> LENGTH: 106
<212> TYPE: PRT
<213> ORGANISM: Human immunodeficiency virus
<220> FEATURE:
<221> NAME/KEY: misc_feature
<223> OTHER INFORMATION: HIV chemokine protein with read-through
      from dual-tropic strain p896 of HIV
<220> FEATURE:
<221> NAME/KEY: Xaa
<222> LOCATION: (28)..(28)
<223> OTHER INFORMATION: Xaa is any amino acid.
<220> FEATURE:
<221> NAME/KEY: Xaa
<222> LOCATION: (38)..(38)
<223> OTHER INFORMATION: Xaa is any amino acid.
<220> FEATURE:
<221> NAME/KEY: Xaa
<222> LOCATION: (73)..(73)
<223> OTHER INFORMATION: Xaa is any amino acid.

<400> SEQUENCE: 20

Met Gln His Leu Arg Ala Arg His Ser Pro Val Arg Pro Arg Pro His
1               5                   10                  15

Leu Pro Gly Lys Ser Pro Ala Glu Ser Pro Leu Xaa Ile Ala Gln Cys
            20                  25                  30

Gln Gln Phe Ser Ser Xaa Ser Thr Pro Asp Ala Ala Leu Gly Pro Arg
        35                  40                  45

Asp Gly Met Leu Gly Gly Cys Gln Thr Ser Thr Leu Thr Leu Val Ser
```

```
            50                  55                  60
Pro Ser Leu Leu His Ala Gly Xaa Gln Gly Val Ala Ser Cys Cys
65                  70                  75                  80

Pro Leu Cys Cys Ser Leu Leu His Leu Ala Gln Leu Val Leu Ala Cys
                85                  90                  95

Ser Thr Ile Gln Arg Ser Val Ile Asp Ile
            100                 105

<210> SEQ ID NO 21
<211> LENGTH: 443
<212> TYPE: RNA
<213> ORGANISM: Human immunodeficiency virus
<220> FEATURE:
<221> NAME/KEY: misc_feature
<223> OTHER INFORMATION: Antisense RNA sequence from pHIV-CAT

<400> SEQUENCE: 21
agaucugguc uaaccagaga gacccaguac aggcaaaaag cagcugcuua uaugcagcau      60
cugagggcuc gccacucccc aguccgccc aggccacgcc uccuggaaa gucccagcg       120 gaaagucccu guaacaagc ucgaugucaa caguucuuga aguaccgg augcagcucu       180 cgggccacgu gaugaaaugc uaggcggcug ucaaaccucc acucuaacac uucucucuca      240
ggucauccca uuccaugcag gcucacaggg uguaacaagc uggu guucuc uccuuuauug      300 gccucuucua ccuuaucugg cucaacuggu acuagcuugu agcaccaucc aaaggucagu      360
ggauaucuga cuccuggccc ugguguguag uucugcuaau cagggaagua gccuugugug      420
ugguagaucc acagaucaag gau                                             443

<210> SEQ ID NO 22
<211> LENGTH: 46
<212> TYPE: PRT
<213> ORGANISM: Human immunodeficiency virus
<220> FEATURE:
<221> NAME/KEY: misc_feature
<223> OTHER INFORMATION: HIV chemokine protein with read-through
      at nucleotides 133-135 from pHIV-CAT
<220> FEATURE:
<221> NAME/KEY: Xaa
<222> LOCATION: (28)..(28)
<223> OTHER INFORMATION: Xaa is any amino acid.

<400> SEQUENCE: 22

Met Gln His Leu Arg Ala Arg His Ser Pro Val Pro Pro Arg Pro Arg
1               5                   10                  15

Leu Pro Gly Lys Ser Pro Ala Glu Ser Pro Leu Xaa Gln Ala Arg Cys
                20                  25                  30

Gln Gln Phe Leu Lys Tyr Ser Gly Cys Ser Ser Arg Ala Thr
            35                  40                  45

<210> SEQ ID NO 23
<211> LENGTH: 35
<212> TYPE: PRT
<213> ORGANISM: Human immunodeficiency virus
<220> FEATURE:
<221> NAME/KEY: misc_feature
<223> OTHER INFORMATION: HIV chemokine protein with (+1) frameshift
      at nucleotide 134 from pHIVCAT

<400> SEQUENCE: 23

Met Gln His Leu Arg Ala Arg His Ser Pro Val Pro Pro Arg Pro Arg
1               5                   10                  15

Leu Pro Gly Lys Ser Pro Ala Glu Ser Pro Leu Asn Lys Leu Asp Val
```

```
                     20                  25                  30

Asn Ser Ser
        35

<210> SEQ ID NO 24
<211> LENGTH: 112
<212> TYPE: PRT
<213> ORGANISM: Human immunodeficiency virus
<220> FEATURE:
<221> NAME/KEY: misc_feature
<223> OTHER INFORMATION: HIV chemokine protein with
      (-1) ribosomal frameshift at nucleotide 133,
      (+1) frameshift at nucleotide 205,
      readthrough at nucleotides 341-343 from pHIVCAT
<220> FEATURE:
<221> NAME/KEY: Xaa
<222> LOCATION: (97)..(97)
<223> OTHER INFORMATION: Xaa is any amino acid.

<400> SEQUENCE: 24

Met Gln His Leu Arg Ala Arg His Ser Pro Val Pro Pro Arg Pro Arg
1               5                   10                  15

Leu Pro Gly Lys Ser Pro Ala Glu Ser Pro Leu Val Thr Ser Trp Met
            20                  25                  30

Ser Thr Val Leu Glu Val Leu Arg Met Gln Leu Ser Gly His Val Met
        35                  40                  45

Lys Cys Arg Arg Leu Ser Asn Leu His Ser Asn Thr Ser Leu Ser Gly
    50                  55                  60

Ser Ser Ile Pro Cys Arg Leu Thr Gly Cys Asn Lys Leu Val Phe Cys
65                  70                  75                  80

Pro Leu Leu Ala Ser Ser Thr Leu Ser Gly Ser Thr Gly Thr Ser Leu
                85                  90                  95

Xaa His His Pro Lys Val Ser Gly Tyr Leu Thr Pro Gly Pro Gly Val
            100                 105                 110

<210> SEQ ID NO 25
<211> LENGTH: 419
<212> TYPE: RNA
<213> ORGANISM: Human immunodeficiency virus
<220> FEATURE:
<221> NAME/KEY: misc_feature
<223> OTHER INFORMATION: antisense RNA sequence from
      an HIV from the CNS of a patient.

<400> SEQUENCE: 25
agaucugguc uaacaagaga gacccaguac aagcgaaaag cagcugcuua uaugcagcau      60
cugagggcac gccacucccg aguccegecc aggccacycc ucccuggaaa gucceccagcg   120 gaaagucccu guagaaagu ucgaugucau caguucuugu aguacuccgg augcagcucu     180
cgggcccugu ggugaaaugc uagggugcug ucaaaucucc acacuaacac uucucucucc    240
gggugcucca ucccaugcag gcacauaggg uguaagauac uguuguucuc uccuucauug    300
ccuucuucua ucuucucugc ucaacuggua cuagcugaaa gcaccauccca aaggucagug   360 gauaucugau cccuggcccu ggugug uagu ugugccaauc agggaaguag ccuugugug     419

<210> SEQ ID NO 26
<211> LENGTH: 419
<212> TYPE: RNA
<213> ORGANISM: Human immunodeficiency virus
<220> FEATURE:
<221> NAME/KEY: misc_feature
<223> OTHER INFORMATION: antisense RNA sequence from an HIV
      from the lymph node and spleen of a patient
```

<400> SEQUENCE: 26

```
agaucugguc uaacuagaga gacccaguac aggcaaagag cagcugcuua uaugcagcau    60
cugagggcac gccacucccg agucccgccc aguccacycc ucccuggaaa gucccccagcg   120 gaaagucccu uguagaaagu ucgaugucau caguucuugu aguagccgg augcagcucu    180 cgggcuacgu ggugaaaugc caggcggcug ucaaaucucc acucuaagac uucucucucc   240
ggguccucca ucccaugcag gcacauagga uguaagaggc uguuguucuc uccuucauug   300
gcuucuucua cuuucucucc ucaacuggua cuagcuuaaa gcaccaucca aaggucagug   360
gauaucugau cccuggcccu ggugaguagu ucugccaauc agggaaguag ccugugug     419
```

<210> SEQ ID NO 27
<211> LENGTH: 367
<212> TYPE: RNA
<213> ORGANISM: Human immunodeficiency virus
<220> FEATURE:
<221> NAME/KEY: misc_feature
<223> OTHER INFORMATION: antisense HAP gene

<400> SEQUENCE: 27

```
agaucugguc uaaccagaga gacccaguac aggcaaaaag cagcugcuua uaugcagcau    60
cugagggcuc gccacucccc agucccgccc aggccacgcc ucccuggaaa gucccccagcg   120 gaaagucccu uguacaagc ucgaugucaa caguucuuga aguacccgg augcagcucu     180 cgggccacgu gaugaaaugc uaggcggcug ucaaaccucc acucuaacac uucucucuca   240 ggucaucca uuccaugcag gcucacaggg uguaacaagc ugguguucuc uccuuuauug   300 gcccucuucua ccuuaucugg cucaacuggu acuagcuugu agcaccaucc aaaggucagu   360
ggauauc                                                              367
```

<210> SEQ ID NO 28
<211> LENGTH: 105
<212> TYPE: PRT
<213> ORGANISM: Human immunodeficiency virus
<220> FEATURE:
<221> NAME/KEY: misc_feature
<223> OTHER INFORMATION: HIV antisense HAP protein translated from
    AUG (nt 52-54) in SEQ ID NO 27, requires a
    (+1) ribosomal frameshift between amino acids 27-28
    and read-through at position 36.
<220> FEATURE:
<221> NAME/KEY: Xaa
<222> LOCATION: (36)..(36)
<223> OTHER INFORMATION: Xaa can be any amino acid.

<400> SEQUENCE: 28

```
Met Gln His Leu Arg Ala Arg His Ser Pro Val Pro Pro Arg Pro Arg
1               5                   10                  15

Leu Pro Gly Lys Ser Pro Ala Glu Ser Pro Leu Asn Lys Leu Asp Val
            20                  25                  30

Asn Ser Ser Xaa Ser Thr Pro Asp Ala Ala Leu Gly Pro Arg Asp Glu
        35                  40                  45

Met Leu Gly Gly Cys Gln Thr Ser Thr Leu Thr Leu Ser Gln Gly
    50                  55                  60

His Pro Phe His Ala Gly Ser Gln Gly Val Thr Ser Trp Cys Ser Leu
65                  70                  75                  80

Leu Tyr Trp Pro Leu Leu Pro Tyr Leu Ala Gln Leu Val Leu Ala Cys
                85                  90                  95

Ser Thr Ile Gln Arg Ser Val Asp Ile
```

-continued

```
                100                 105

<210> SEQ ID NO 29
<211> LENGTH: 108
<212> TYPE: PRT
<213> ORGANISM: Human immunodeficiency virus
<220> FEATURE:
<221> NAME/KEY: misc_feature
<223> OTHER INFORMATION: HIV antisense HAP protein translated from
      CUG alternate start site in SEQ ID NO 27 (nt 44-46) ;
      requires read-through at positions 7 and 39.
<220> FEATURE:
<221> NAME/KEY: Xaa
<222> LOCATION: (7)..(7)
<223> OTHER INFORMATION: Xaa can be any natural amino acid
<220> FEATURE:
<221> NAME/KEY: Xaa
<222> LOCATION: (39)..(39)
<223> OTHER INFORMATION: Xaa can be any natural amino acid

<400> SEQUENCE: 29

Met Leu Ile Cys Ser Ile Xaa Gly Leu Ala Thr Pro Gln Ser Arg Pro
1               5                   10                  15

Gly His Ala Ser Leu Glu Ser Pro Gln Arg Lys Val Pro Cys Asn Lys
            20                  25                  30

Leu Asp Val Asn Ser Ser Xaa Ser Thr Pro Asp Ala Ala Leu Gly Pro
        35                  40                  45

Arg Asp Glu Met Leu Gly Gly Cys Gln Thr Ser Thr Leu Thr Leu Leu
    50                  55                  60

Ser Gln Gly His Pro Phe His Ala Gly Ser Gln Gly Val Thr Ser Trp
65                  70                  75                  80

Cys Ser Leu Leu Tyr Trp Pro Leu Leu Pro Tyr Leu Ala Gln Leu Val
                85                  90                  95

Leu Ala Cys Ser Thr Ile Gln Arg Ser Val Asp Ile
            100                 105

<210> SEQ ID NO 30
<211> LENGTH: 109
<212> TYPE: PRT
<213> ORGANISM: Human immunodeficiency virus
<220> FEATURE:
<221> NAME/KEY: misc_feature
<223> OTHER INFORMATION: HIV antisense HAP protein (clade A)
      translated from CUG alternate start site;
      requires read-through at positions 7 and 40.
<220> FEATURE:
<221> NAME/KEY: Xaa
<222> LOCATION: (7)..(7)
<223> OTHER INFORMATION: Xaa is any natural amino acid.
<220> FEATURE:
<221> NAME/KEY: Xaa
<222> LOCATION: (40)..(40)
<223> OTHER INFORMATION: Xaa is any natural amino acid.

<400> SEQUENCE: 30

Met Leu Ile Cys Ser Ile Xaa Gly Leu Ala Thr Pro Gln Leu Arg Pro
1               5                   10                  15

Asn His Thr Ser Pro Gly Lys Ser Pro Ala Glu Ser Pro Cys Gln Gln
            20                  25                  30

Leu Leu Cys Gln Gln Ser Leu Xaa Asn Ser Gly Cys Ser Ser Arg Ala
        35                  40                  45

Leu Cys Phe Ser Ala Arg Arg Leu Ser Asn Phe His Ile Asn Val Ser
    50                  55                  60

Leu Ser Ser Ser Ile Pro Cys Trp His Ile Gly Cys Asn Arg Leu
65                  70                  75                  80
```

```
Leu Phe Ser Pro Ser Val Ser Phe Ser Thr Ser Ser Gly Ser Thr Gly
                85                  90                  95

Thr Ser Leu Lys His His Pro Asn Val Ser Gly Tyr Leu
            100                 105
```

<210> SEQ ID NO 31
<211> LENGTH: 152
<212> TYPE: PRT
<213> ORGANISM: Human immunodeficiency virus
<220> FEATURE:
<221> NAME/KEY: misc_feature
<223> OTHER INFORMATION: HIV antisense HAP protein translated from
      AUG start: requires (-1) ribosomal frameshift
      between amino acids 48 and 49.
<220> FEATURE:
<221> NAME/KEY: misc_feature
<223> OTHER INFORMATION: HIV clade A.

<400> SEQUENCE: 31

```
Met Gln His Leu Arg Val Ser His Ser Pro Thr Pro Pro Lys Pro His
1               5                   10                  15

Leu Pro Trp Lys Val Pro Ser Gly Lys Ser Leu Ser Ala Thr Ser Val
            20                  25                  30

Ser Ala Val Phe Val Asp Leu Arg Met Gln Leu Ser Gly Ser Val Phe
        35                  40                  45

Glu Val Pro Gly Gly Cys Gln Thr Ser Thr Leu Met Phe Leu Ser Leu
    50                  55                  60

His His Pro Phe His Val Gly Ile Trp Gly Val Ile Gly Cys Cys Ser
65                  70                  75                  80

Leu Pro Gln Tyr Pro Ser Leu Leu His Leu Asp Gln Leu Val Leu Ala
                85                  90                  95

Cys Ser Thr Ile Gln Met Leu Val Gly Ile Trp Ser Leu Ala Leu Val
            100                 105                 110

Cys Asn Ser Ala Asn Gln Gly Ser Ser Leu Val Cys Gly Arg Pro Thr
        115                 120                 125

Asp Gln Gly Phe Leu Val Phe Ser Trp Ser Lys Leu Thr His Pro Val
    130                 135                 140

Pro Pro Phe Leu Leu Lys Ser Gly
145                 150
```

<210> SEQ ID NO 32
<211> LENGTH: 509
<212> TYPE: RNA
<213> ORGANISM: Human immunodeficiency virus
<220> FEATURE:
<221> NAME/KEY: misc_feature
<223> OTHER INFORMATION: HIV antisense HAP gene (clade A).

<400> SEQUENCE: 32

```
agaucuggnc uaacaagaga gacccaguac aggcgaaaag cagcugcuua uaugcagcau    60
cugaggguua gccacucccc aacuccgccc aaaccacacc uccccuggaa aguccccagc   120
ggaaagnccc ugucagcaac uucuguguca gcagucuuug uagaacuccg gaugcagcuc   180
ucgggcucug uguuuagng ccaggcggcu gucaaacuuc acuuuaaug uuucucucuc     240 uucaucaucc auccaugunu ggcauauagg guguaauagg cuguuguucu cucccucagu   300
auccuucucu acuucaucug gaucaacugg uacuagcuug aagcaccauc caaauguuag   360
ugggnaucug gucccuggcc cuggugugua auucugccaa ucagggaagu agccuugngu   420
gungnagacc cacagaucaa ggauuucuug ucuuuuccug gaguaaauua acccauccag   480
```

```
uccccccuuu ucuuuuaaaa aguggcuga                                      509
```

<210> SEQ ID NO 33
<211> LENGTH: 90
<212> TYPE: PRT
<213> ORGANISM: Human immunodeficiency virus
<220> FEATURE:
<221> NAME/KEY: misc_feature
<223> OTHER INFORMATION: HIV antisense HAP gene (long-term survivors).

<400> SEQUENCE: 33

Met Gln His Leu Arg Ala Arg His Ser Pro Val Pro Pro Arg Pro Arg
1               5                   10                  15

Leu Leu Gly Lys Ser Pro Pro Glu Leu Val Thr Gln Ala Thr Pro Pro
            20                  25                  30

Trp Lys Val Pro Asn Gly Trp Lys Val Pro Asn Arg Arg Ile Cys Gly
        35                  40                  45

Phe Leu Leu His Trp Pro Leu Leu Ser Ser Leu Thr Pro Leu Val Ile
    50                  55                  60

Val Cys Ser Thr Val Tyr Leu Val Phe Phe Gly Ser Glu Leu Ala Leu
65                  70                  75                  80

Pro Val Pro Pro Phe Leu Leu Lys Ser Gly
            85                  90

<210> SEQ ID NO 34
<211> LENGTH: 560
<212> TYPE: RNA
<213> ORGANISM: Human immunodeficiency virus
<220> FEATURE:
<221> NAME/KEY: misc_feature
<223> OTHER INFORMATION: HIV antisense HAP gene (C clade).

<400> SEQUENCE: 34

```
agaucugguc uaccuagaga gacccaguac aggcgaaaag cagcugcuua uaugcagcau    60
cugaggguug accacucccc aguccccgccc agaccacacc uccuggaacg ccccagugga   120 aaguccccagc ggaaagucccc uucuguguca gcagucuuug uaauacuccg gauguagcuc   180
gcgggccaug ugucugcgug cuaggugacu gucaaacuuc cacuuuaaua cuucucugug    240
uucauccucc auccauccu ggcucacagg guguagcaaa caguugucuu uccuucguu     300 ggcucuucu acuucccuug ggucaacugg uacuagcuug uagcaccauc caaaggucag    360
uggguaucug gccccuigguc ccggugugua guuuugccaa ucaggaaga agccuugugu    420 gugauugucc cacaaaucaa ggaucucuug ccuuucuug gaguaaauua acccuuccag    480 ucccccuu ucuuuaaaa agaagccgag aucgaaugcu cccuuauaag ucauuggucu     540
uaaaggcacc ugaggucuga                                                560
```

<210> SEQ ID NO 35
<211> LENGTH: 168
<212> TYPE: PRT
<213> ORGANISM: Human immunodeficiency virus
<220> FEATURE:
<221> NAME/KEY: misc_feature
<223> OTHER INFORMATION: HIV antisense HAP protein from
      first AUG in SEQ ID NO 34 (C clade).

<400> SEQUENCE: 35

Met Gln His Leu Arg Val Asp His Ser Pro Val Pro Pro Arg Pro His
1               5                   10                  15

Leu Leu Glu Arg Pro Ser Glu Ser Pro Ser Ala Lys Ser Leu Leu Cys

-continued

```
            20                  25                  30

Gln Gln Ser Leu Asn Thr Pro Asp Val Ala Arg Gly Pro Cys Val Cys
        35                  40                  45

Val Leu Gly Asp Cys Gln Thr Ser Thr Leu Ile Leu Leu Cys Val His
    50                  55                  60

Pro Pro Phe His Ala Gly Ser Gln Gly Val Ala Asn Ser Cys Leu Leu
65                  70                  75                  80

Leu Arg Trp Pro Leu Leu Leu Pro Leu Gly Gln Leu Val Leu Ala Cys
                85                  90                  95

Ser Thr Ile Gln Arg Ser Val Gly Ile Trp Pro Leu Val Pro Val Cys
            100                 105                 110

Ser Phe Ala Asn Gln Gly Arg Ser Leu Val Cys Asp Cys Pro Thr Asn
        115                 120                 125

Gln Gly Ser Leu Ala Phe Ser Trp Ser Lys Leu Thr Leu Pro Val Pro
    130                 135                 140

Pro Phe Leu Leu Lys Arg Ser Arg Asp Arg Met Leu Pro Tyr Lys Ser
145                 150                 155                 160

Leu Val Leu Lys Ala Pro Glu Val
                165

<210> SEQ ID NO 36
<211> LENGTH: 14
<212> TYPE: PRT
<213> ORGANISM: Human immunodeficiency virus
<220> FEATURE:
<221> NAME/KEY: misc_feature
<223> OTHER INFORMATION: portion of HAP protein used to
      raise antibodies in rabbits.

<400> SEQUENCE: 36

Asp Ala Ala Leu Gly Pro Arg Asp Glu Met Leu Gly Gly Cys
1               5                   10
```